United States Patent [19]

Atkinson

[11] Patent Number: 4,655,197

[45] Date of Patent: Apr. 7, 1987

[54] LAVAGE SYSTEM WITH VARIABLE FREQUENCY, FLOW RATE AND PRESSURE

[75] Inventor: Robert W. Atkinson, Dover, Ohio

[73] Assignee: Snyder Laboratories, Inc., Dover, Ohio

[21] Appl. No.: 445,793

[22] Filed: Dec. 1, 1982

[51] Int. Cl.⁴ ............................................. A61H 9/00
[52] U.S. Cl. ................................. 128/66; 128/24 A; 604/30; 604/150
[58] Field of Search ................. 128/66, 24 A; 604/30, 604/31, 22, 118, 119, 150, 152; 417/326

[56] References Cited

U.S. PATENT DOCUMENTS

| | | | |
|---|---|---|---|
| 2,246,932 | 6/1941 | Collins | 417/62 |
| 3,433,983 | 3/1969 | Keistman et al. | 310/15 |
| 3,537,444 | 11/1970 | Gara | 128/66 |
| 3,589,363 | 6/1971 | Banko et al. | 604/27 X |
| 3,610,782 | 10/1971 | McGuire, III | 417/326 |
| 3,762,648 | 10/1973 | Deines et al. | 239/383 |
| 3,801,019 | 4/1974 | Trenary et al. | 239/383 |
| 3,870,039 | 3/1975 | Moret et al. | 128/66 |
| 3,958,756 | 5/1976 | Trenary et al. | 239/102 |
| 3,982,540 | 9/1976 | Ross | 128/278 |
| 4,190,207 | 2/1980 | Fienhold et al. | 239/381 |
| 4,215,476 | 8/1980 | Armstrong | 433/80 |
| 4,282,873 | 8/1981 | Roth | 128/276 |
| 4,299,221 | 11/1981 | Phillips et al. | 128/276 |
| 4,350,477 | 9/1982 | Mazal | 417/384 |

FOREIGN PATENT DOCUMENTS 1602277 11/1981 United Kingdom .

OTHER PUBLICATIONS

Stryker® advertisement, "Excerpts from Clinical Studies".
Single page Stryker® ad, "Introducing SysTec ™ 280 Suction/Irrigation/Nitrogen Power System".
Pamphlet "SysTec ™ 280 Suction/Irrigation Nitrogen Power System".
Stryker® pamphlet, "SysTec ™ 280 Suction/Irrigation Nitrogen Power System".
Stryker® manual, "SysTec ™ 280".
Gross, A. et al., The Effects of Pulsating Water Jet Lavage on Experimental Wounds, J. Oral Surg. 29:187, Mar. 1971.
Bhaskar, S. N. et al., Pulsating Water Jet Device in Debribement of Combat Wounds, Melit Med. 136:264, Mar. 1971.
MacIntash, D. et al., Joint Debribement, A Compliment to High Tibeal Osleotomy in the Treatment of Degenerative Arthritis of the Knee, JBJS 59A #8:1094, 12/77.
Haury, B. et al., Debribement: An Essential Component of Traumatic Wound Care, Am. J. of Surg. 135:238, Feb. 1978.
Grower, M. et al., Effect of Water Lavage on Removal of Tissue Fragments from Crash Wounds, Oral Surg., Jun. 1972.

Primary Examiner—Richard J. Apley
Assistant Examiner—J. Welsh
Attorney, Agent, or Firm—Paul David Schoenle

[57] ABSTRACT

A mechanism, such as a motor driving a pump, creates a pulsating fluid flow. There is a control for varying the pulsation frequency independently of the fluid pressure or rate of flow. Another control varies the pressure or rate of fluid flow independently of the frequency of pulsation. Separate pulsatile lavage, irrigation, and aspiration functions are provided. In another aspect, the mechanism for producing the pulsating flow includes a fluid driving means, such as a reciprocating pump, and there is a means for varying the length of stroke of the driving means.

3 Claims, 26 Drawing Figures

IRRIGATION METER COMPONENTS

- A  CONNECTOR WTB10PR7JTA
- B  .22μF CAPACITOR
- C  47 K RESISTOR
- D  .47μF CAPACITOR
- E  .01μF CAPACITOR
- F  1 MEG RESISTOR
- G  .1μF CAPACITOR
- H  100 K RESISTOR
- J  100 PF CAPACITOR
- K  ICL7106CP CHIP
- L  40 PIN SOCKET
- M  26 PIN HEADER
- N  26 PIN CABLE
- P  1K 15 TURN POT
- Q  24 K RESISTOR
- R  2 MEG 15 TURN POT
- *  CABLE LOCATOR

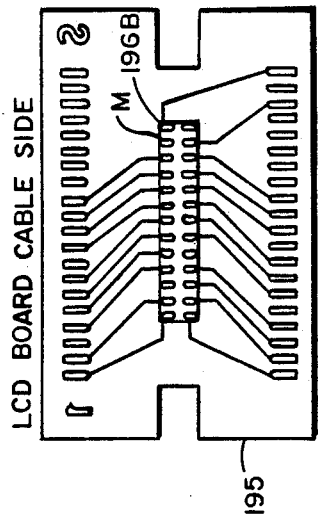
FIG.11K₁
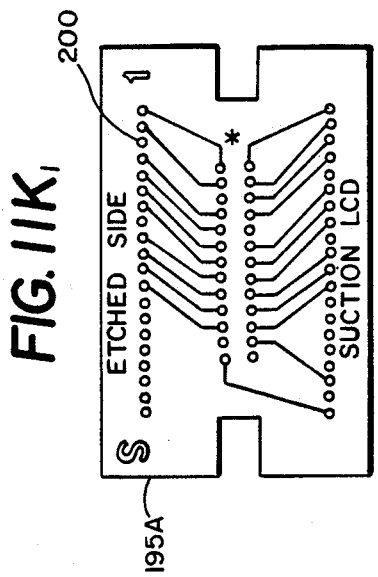
FIG.11K₂
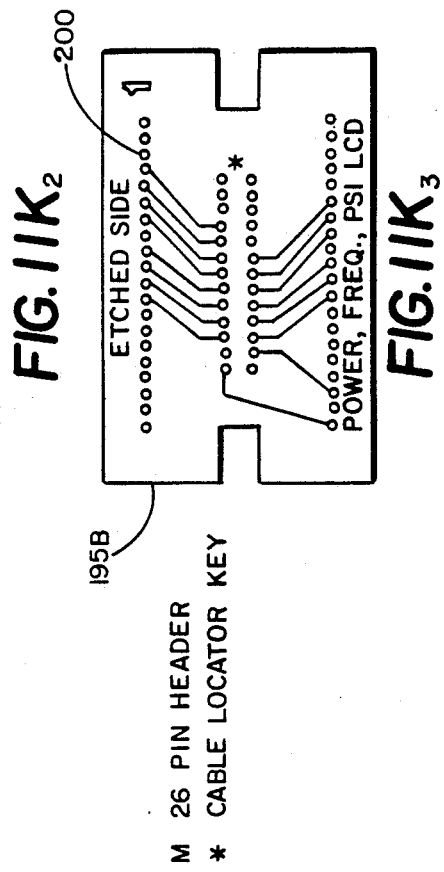
FIG.11K₃
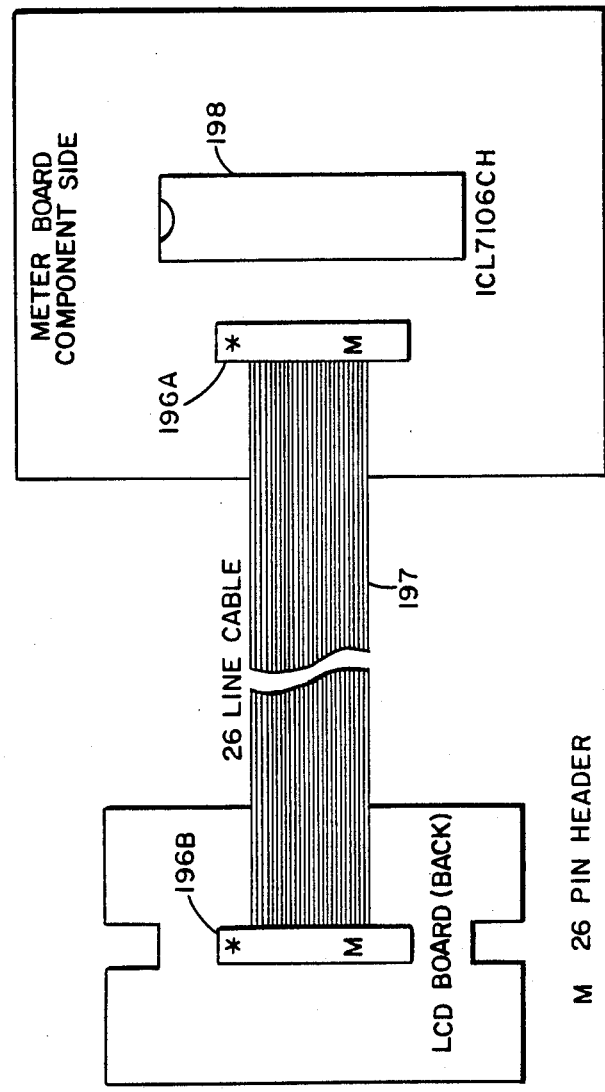
FIG.11J₁
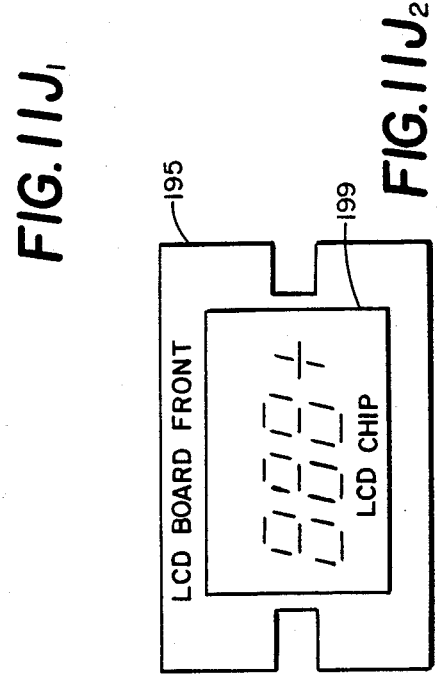
FIG.11J₂

SUCTION TRANSDUCER COMPONENTS

A. FOXBORO 1800 TRANSDUCER
B. BALANCE RESISTOR

LAVAGE SYSTEM WITH VARIABLE FREQUENCY, FLOW RATE AND PRESSURE

BACKGROUND OF THE INVENTION

1. Field of the Invention

The invention in general relates to the field of medical, dental and therapeutic lavage, and more particularly to a mechanized lavage system in which the rate of fluid flow and the average fluid pressure, are variable.

2. Description of the Prior Art

Lavage, or the washing of tissue, is perhaps as old as medicine itself. In the early years it consisted of the application of fluid, generally a liquid such as water, to tissue to wash away dirt or debris. In more modern times, it has become more important, and more thorough, due to an awareness of bacteria and other organisms that may cause infection. In the last several decades, mechanized lavage systems have become common.

Before proceeding to the discussion of prior art mechanized devices it will be useful to clarify terminology. The word "lavage" is used ambiguously in the literature, sometimes referring to a pulsating stream type washing or therapy, sometimes referring to a stream type of washing, and sometimes also including an aspiration function. In this document, unless the context clearly indicates otherwise, "irrigation" shall mean the stream type of washing "pulsatile lavage" shall mean the pulsating type of washing, and the word "lavage" shall mean the broadest sense of the term, referring to any one of, or combinations of, irrigation, pulsatile lavage, and aspiration.

It will also be useful to note that in a system in which fluid is caused to flow through a tube, that the pressure of the fluid and the rate of fluid flow change in the same way. For example, if the pressure increases then so does the rate of flow, and if the rate of flow increases then so does the pressure. Thus some of the basic aspects of the invention, for example the controllability and variability aspects, may be discussed in terms of either rate of flow or in terms of pressure.

In addition, it is helpful to note that when the word pressure is used herein it will normally refer to the average pressure along a fluid stream in contrast to the instantaneous pressure which will vary in a stream having pulsations.

Mechanical lavage systems are disclosed in U.S. Pat. No. 3,540,437 issued to Troy, U.S. Pat. No. 3,912,168 issued to Mullins et al., U.S. Pat. No. 3,993,054 issued to Newman, U.S. Pat. No. 4,278,078 issued to Smith, and U.S. Pat. No. 4,294,251 issued to Greenwald et al. All the foregoing patents disclose apparatus for producing a pulsating fluid lavage stream in which the pulsation is fixed at a single frequency. Conceivably, other frequencies might be obtained with these systems by changing the frequency of rotation or reciprocation of the motors, although clearly under such circumstances the rate of fluid flow and pressure would change considerably as the frequency changed. U.S. Pat. No. 3,902,664 issued to Deines discloses a fluid pulsator in which the frequency of pulsation may be changed. Analysis of the system indicates that the change of frequency is accomplished by changing the back pressure created in the device and thereby altering the rate of flow of fluid through the device. In the latter patent it appears that although the instantaneous pressure within each individual pulse as it energes from the exit valve of the pulsating mechanism may remain approximately constant throughout a wide range of frequencies, it is also evident that the average pressure of the fluid flow will change considerably over the frequency range since the rate of fluid flow changes considerably. Furthermore, as the individual pulses move away from the exit valve of the pulsation creating device, the change in average pressure will cause the instantaneous pressure within each pulse to change well before it leaves the lavage tube.

Generally, the most modern medical lavage and irrigation systems have included suction (aspiration) functions for removing the lavage fluid. See for example U.S. Pat. No. 4,299,221 issued to Phillips et al. and U.S. Pat. No. 4,294,251 issued to Greenwald et al. This suction function has been found to be useful and necessary to remove the lavage fluid to create a clear field, for example, when the lavage is used to cleanse a wound during surgery, and also to remove the debris when pulsatile lavage is used for debridement purposes.

It appears that, in general, prior art medical lavage systems have been limited to single frequencies since the sudden and unpredictable change in fluid flow caused by the changing frequency in all prior art systems can cause considerable problems. For example, both the too much fluid and too little fluid situations can interfere with surgery, which could be serious if it occurred at critical times. As we will be seeing, the removal of this limitation by the present invention has resulted in many surprising advantages of having a variable frequency being discovered.

In the prior art, as well as in the present invention, if the rate of flow through the lavage system is changed, the average pressure of the fluid stream will also change, as long as the tubing and other parts constricting the flow remain unchanged in diameter. This normally causes little problem since the relationship between pressure and flow is a familiar one due to the almost constant contact with such pressurized flow systems, such as the faucet, etc., in the modern environment. Accordingly, most prior art lavage and irrigation systems include a means for altering the rate of flow (fluid pressure) of the system. Such controls appear to be universally of the throttle type control. See any of the above-cited patents. The throttle type control necessarily is inefficient since it causes the motor providing the irrigation or lavage function to waste energy as the motor struggles to force the fluid through a constricted opening. In most systems, the result is that the motor is ironically forced to produce the highest pressures precisely at the time when reduced pressure at the lavage head is used. In addition to wasted energy, such throttle systems result in shortened life for mechanical parts, and considerably increased operating noise of the system. These factors were perhaps not seen as disadvantages in the prior art system; however it has been found that the present invention has removed these characteristics in a unexpected and thorough fashion that now reveals them to be quite undesirable, when the controllability, quietness and efficiency of the lavage and irrigation system of the present invention is compared to the prior art.

SUMMARY OF THE INVENTION

It is an object of this invention to provide a lavage system having a pulsatile lavage function. It is another object of the invention to provide a system having an irrigation function. It is a further object of the invention to provide a system having a suction function. It is a fourth object of the invention to provide a system having a combination of any of the above functions.

Another object of the invention is to provide a lavage system in which the rate of fluid flow or the pressure may be varied by varying the length of stroke of the fluid driving means.

A further object of the invention is to provide a lavage system in which the frequency may be varied over a wide range without altering the rate of fluid flow or fluid pressure. Another object of the invention is to provide a lavage system in which the rate of fluid flow or fluid pressure may be varied over a wide range without altering the pumping frequency of the irrigation and suction functions, and without altering the fluid pulsation frequency of the pulsatile lavage function.

Yet another object of the invention is to provide a lavage system having a pulsatile lavage mode in which the frequency and rate of flow (pressure) are separately controllable and settable, and an irrigation mode in whcih the pulsation frequency of the fluid stream is fixed and may be ignored while the rate of flow or pressure may be varied.

It is still another object of the invention to achieve one or more of preceding objects in the lavage system having high energy efficiency.

It is a further object of the invention to achieve one or more of the preceding objects in a lavage system that is unusually quiet while functioning.

Still another object of the invention is to provide a lavage system in which the fluid pulsation frequency, the rate of fluid flow, the average fluid pressure, and the pumping frequency each may be controlled with high accuracy.

It is yet another object of the invention to provide a system that achieves one or more of the preceding objects and is highly reliable.

The invention comprises a lavage apparatus which included a means for producing a pulsating fluid flow, and a means for varying the pulsation frequency of the fluid flow while maintaining the pressure or rate of fluid flow substantially constant. Preferably the lavage apparatus also includes a means for varying the fluid pressure or the rate of fluid flow while maintaining the pulsation frequency constant. The preferred system also includes a means for fixing the frequency at a predetermined frequency, a switch having a first position in which the means for varying the frequency is enabled to control the pulsation frequency and a second position in which the means for fixing the frequency is enabled to control the pulsation frequency, and wherein the means for varying the pressure or rate of fluid flow includes a first manually settable control for controlling the pressure or rate of fluid flow and a second manually settable control for controlling the pressure or rate of flow and the switch switches control of the pressure or rate to the first control when the switch is in the first position and switches control of the pressure or rate to the second control when the switch is in the second position. In another aspect of the invention, the invention comprises a medical, dental or therapeutic lavage system of the type having a chamber having an inlet and an outlet, a means for imparting a flow to fluid moving from the inlet to the outlet within the chamber, and a means for varying the pressure or rate of fluid flow characterized by the improvement comprising the means for imparting including a fluid driving means moving along a repetitive stroke, and the pressure or rate varying means including a means for varying the length of stroke of the fluid driving means.

It has been found that the lavage system provided by the invention is surprisingly effective in removing debris from a wide range of tissues. It is believed that this is due to the fact that various tissues have different natural frequencies of vibration and that the optimum pulsation frequency for debridement is related to these natural frequencies, and thus the ability to accurately control the pulsation frequency permits optimization of the debridement function for a wide variety of tissues for which this was not previously possible. The ability to accurately control rate of flow, while the frequency is being varied to find the optimum frequency, greatly enhances the ability of the physician to find the proper frequency since the situation is not complicated by a simultaneously changing flow. Further, it has been discovered that the quietness of the machine makes it significantly more welcome in the hospital and other medical therapeutic environments.

Numerous other features, objects and advantages of the invention will now become apparent from the following detailed description when read in conjunction with the accompanying drawings, in which:

BRIEF DESCRIPTION OF THE DRAWINGS

FIGS. 11A thru 11L show more detailed electrical diagrams of the various portions of the electronics of FIGS. 10A and 10B;

DESCRIPTION OF THE PREFERRED EMBODIMENT

Figure 1:
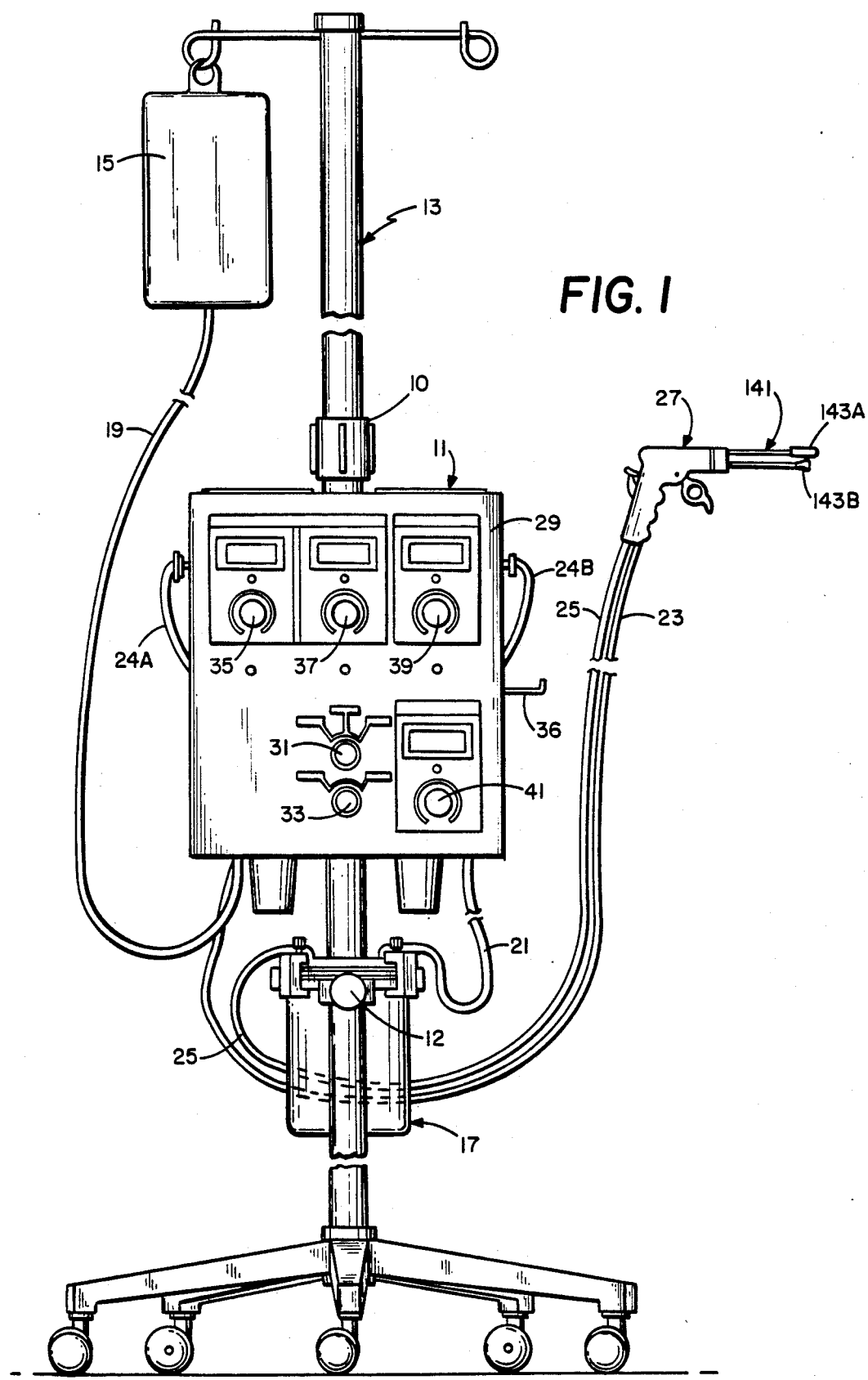
FIG. 1 is a front view of a lavage system in accordance with a preferred embodiment of the invention.
Figure 2:
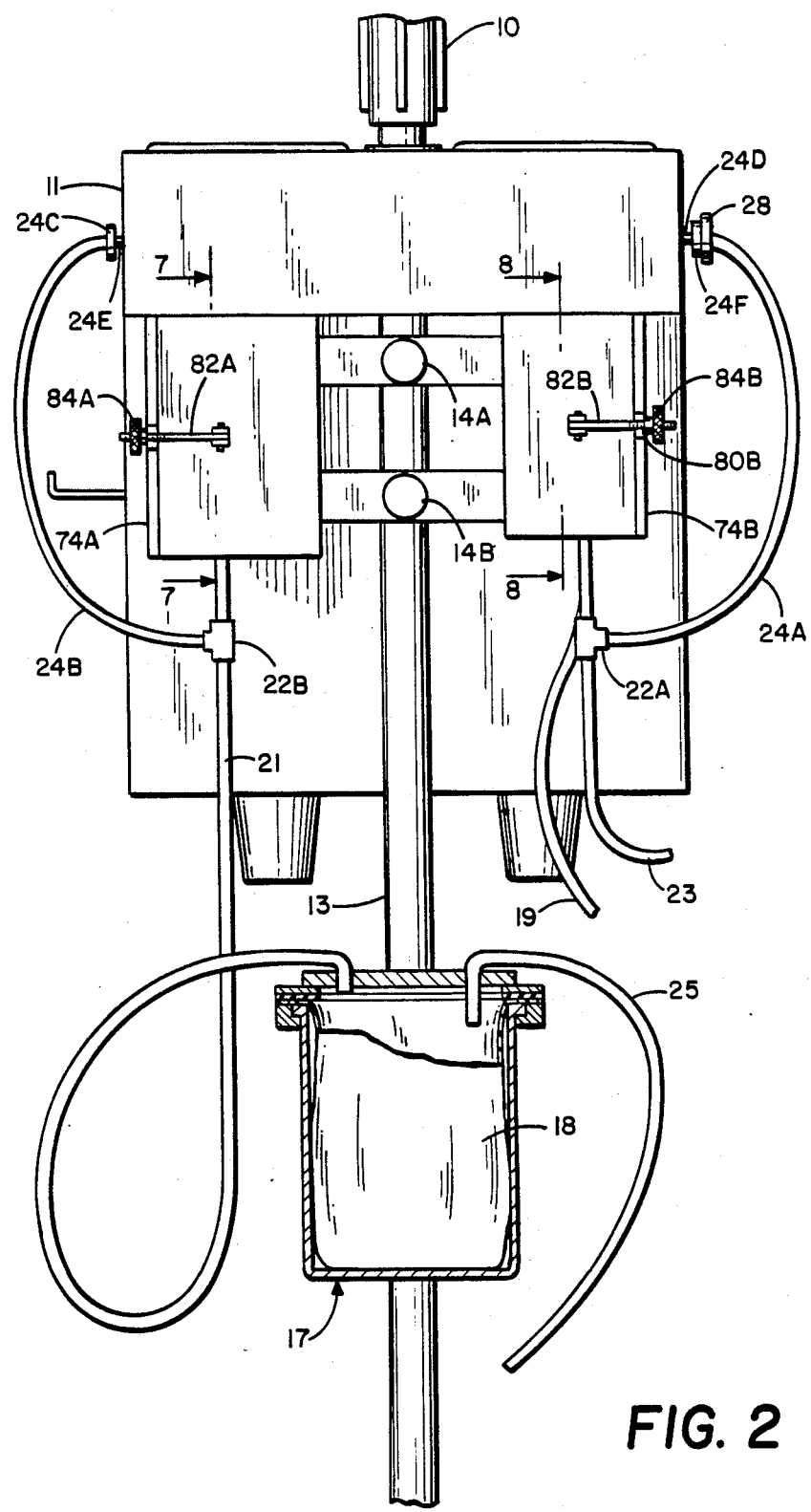
FIG. 2 is a partial rear view of the lavage system of FIG. 1.
Figure 3:
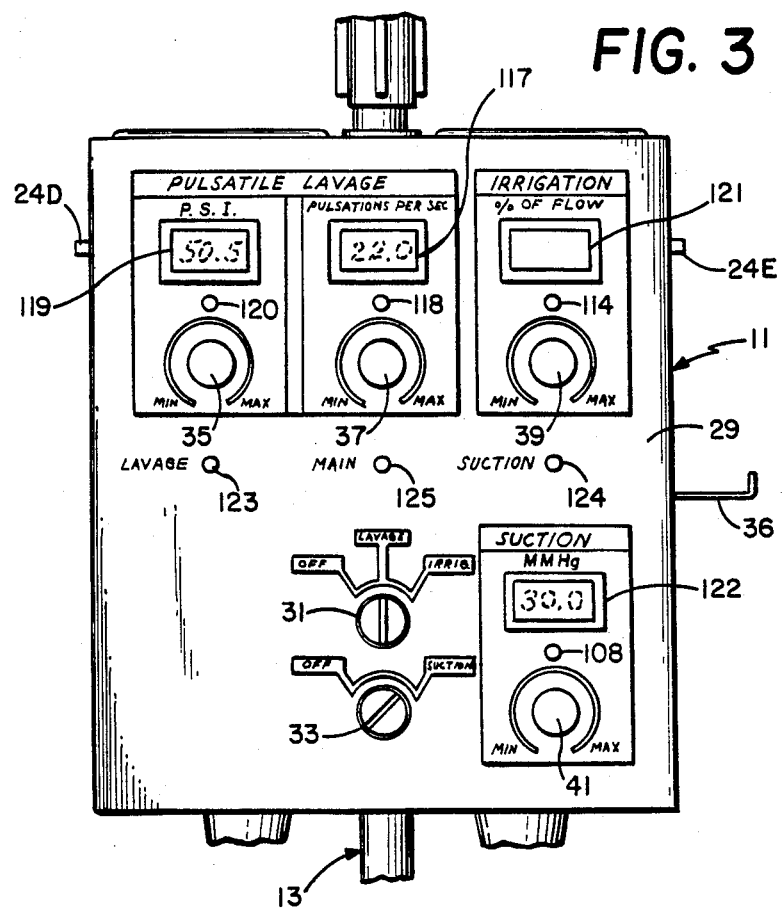
FIG. 3 is a front view of the housing for the lavage system of FIG. 1.

Referring to FIGS. 1-3, external views of the lavage system according to this invention are shown. The system includes a housing 11 mounted on a movable stand 13 along with a supply 15 of fluid such as saline solution. Below the housing 11 and also mounted to the stand 13 is a drainage tank 17. The fluid supply 15 is connected to a pulsatile lavage/irrigation pump 51A (not shown in these figures) in the housing 11 by line 19, and the drainage tank 17 is likewise connected to a suction pump 51B (also not shown) in the housing 11 by line 21. The pumps will be described later. A pulsatile lavage/irrigation fluid line 23 connects the pump 51A to a lavage handpiece 27 to provide a stream of fluid at nozzle 143B. A suction line 25 connects the lavage handpiece 27 to the drainage tank 17. The vacuum line 21, connecting the drainage tank 17 to the suction pump 51B in the housing 11, provides fluid suction at the nozzle 143A via line 25.

The housing 11 contains circuitry and pumps which provide pulsatile lavage and irrigation functions by pumping fluid from the supply 15 to the lavage head 27 via line 23 and provide an aspirating function by pumping fluid from the lavage head 27 via line 25 to the drainage tank 17 by providing vacuum at line 21. Hereinafter in this description, for simplicity and to avoid suggesting that there may be more than two pumps, we shall refer to the pump and the associated components which provide both the pulsatile lavage and irrigation functions by the designation PL/IR.

Referring to FIG. 3, the pulsatile lavage, irrigation and suction functions are controlled at control board 29. A pair of switches 31, 33 operate the PL/IR and suction pumps, respectively. The suction control switch 33 is a two-position on/off switch, while the PL/IR control switch 31 is a three-position switch having an "off" position, a "lavage" (here short for pulsatile lavage) position and an "irrigation" position. The PL/IR control switch 31 is used to switch the PL/IR motor from "off" to "lavage" and "irrigation" control modes with "lavage" mode control being effected by control knobs 35 and 37 and "irrigation" mode control being effected by knob 39. In this embodiment the suction pump is operable in only a single "suction" mode which is controlled by knob 41.

It can be seen that the system can be controlled in three "on" modes: "lavage," "irrigation," and "suction." Further, "lavage" when used in connection with knob 31 is short for the term pulsatile lavage used elsewhere herein. Moreover, both the "lavage" and "irrigation" modes provide irrigation in the sense that they both provide a stream of liquid. Likewise, while in the present embodiment the "lavage" mode does not control suction, suction is generally considered to be an integral part of surgical lavage. For this reason, the choice of terminology chosen to distinguish the three functions of the preferred system should not be considered to be limiting when these terms are used in somewhat different senses in other contexts.

Having provided a brief orientation to the drawings and the functions of the preferred system we shall now return to FIGS. 1 and 2 and proceed with a more detailed description.

Stand 13 includes a collar 10 for adjusting the height of the upper portion, and thus the height of fluid supply, above the housing 11. Housing 11 includes knobbed set screws 14A and 14B for adjusting its height on stand 13. Drainage tank 17 also includes a knobbed set screw 12 for adjustment of its height.

Figures 5, 6:
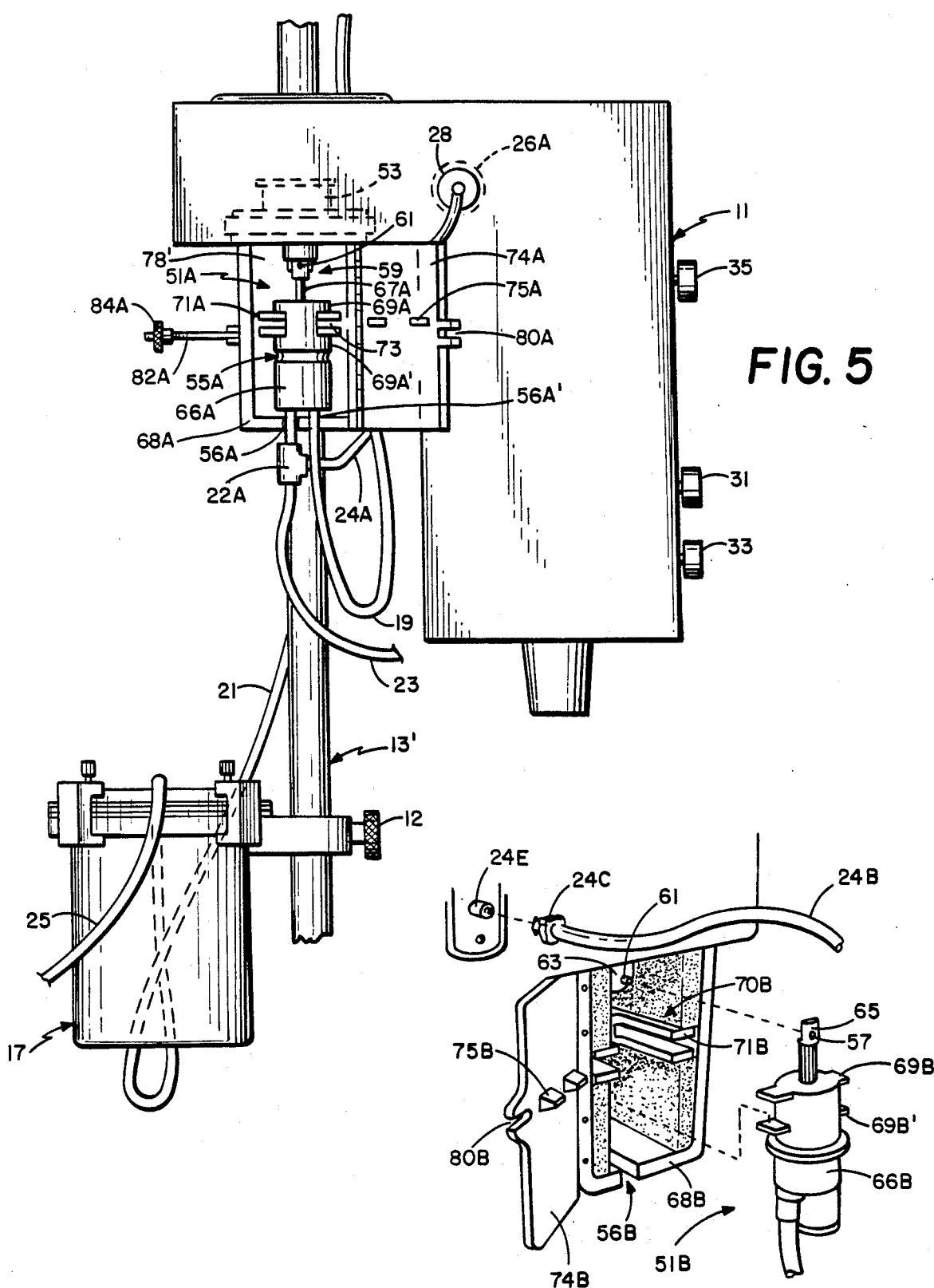
FIG. 5 is a side view of the housing of FIG. 3 showing the preferred pulsatile lavage/irrigation pumping chamber.
FIG. 6 is a side view of the housing showing the suction pumping chamber, and indicating the manner of insertion of the pump.

We have already described the connection of tubes 19, 21, 23, and 25. The system also includes tubes 24A and 24B. One end of line 24A connects to "T" 22A in line 23 and the other end connects to the pressure transducer coupling 24D. The connection is made by means of a leur lock connector 24F having a filter 28 attached to prevent contamination of the fluid in tube 23 by transducer 26A (FIG. 5). One end of line 24B connects to "T" 22B in line 21 and the other end connects to suction transducer coupling 24E via leur lock connector 24C. The transducers 26A and 26B will be discussed in more detail in connection with FIG. 9. Also shown in FIG. 2 is a disposable drainage bag 18 which optionally fits within tank 17. In a third alternative of the drainage system bag 18 may be replaced by a disposable rigid cannister.

Figure 4:
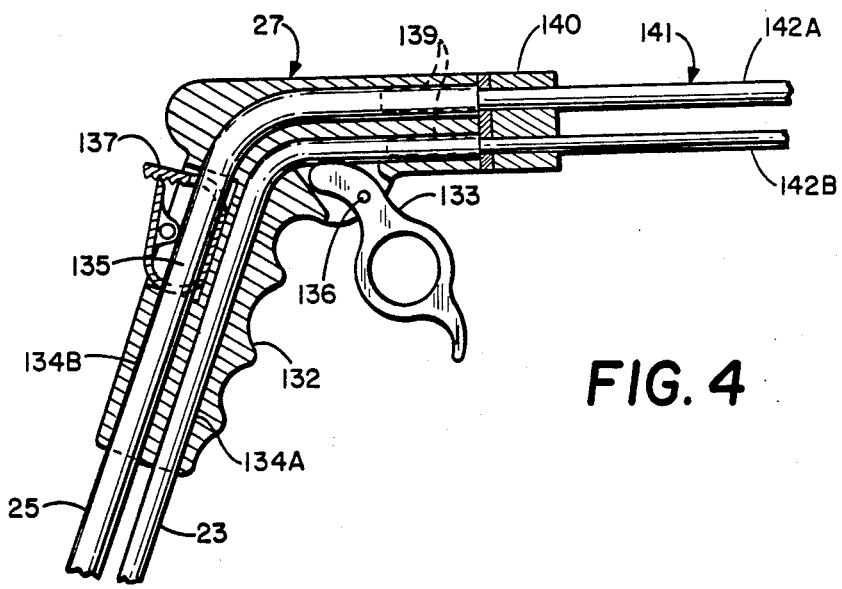
FIG. 4 is a sectional view of the preferred embodiment of the lavage handpiece.

Referring to FIG. 4, the lavage handpiece 27 in the preferred embodiment includes a pistol-shaped body 132 and a pair of pinch valves 133 and 135, which are secured in hollows molded in body 132. A pair of cylindrical channels 134A and 134B are formed within body 132 of an appropriate size to accept the ends of tubing 23 and 25. Pinch valve 133 is rotatable about pin 136 to pinch off tubing 23. Serrated arm 137 holds pinch valve 135 in an open or closed position. It is made of a flexible material so that it may be raised upward to release pinch valve 135 as desired. Attached to the lavage handpiece 27 is a nozzle tube assembly 141 which comprises two semi-rigid tubes 142A and 142B held in a plug 140, and a pair of nozzles 143A and 143B (FIG. 1) attached to the ends of tubes 142A and 142B respectively. The proximal ends of tubes 142A and 142B fit into the open ends 139 of tubes 23 and 25. In the preferred embodiment these nozzles and tubes form a replaceable assembly, which is described in detail in a companion application. Since the particular form of the nozzles are not a part of this invention they will not be discussed further herein.

Referring to FIGS. 5–8, the pulsatile lavage/irrigation pump 51A and suction pump 51B are shown. Each pump 51A and 51B is attached to an electric driving motor, which in the preferred embodiment is a linear reciprocating motor; however, only one motor 53 is shown (attached to pump 51B) as the other motor is identical. Each motor, such as 53, is connected to its pump, such as 51B, by a coupling 59. Each coupling 59 consists of a pin 61 and a pair of flange sections 63, 65 associated with the motors 53 and pumps (51A or 51B) respectively. Each pin 61 is located on the motor flange 63 and inserts into a hole 57 in the pump flange 65. Each flange 65 is connected to a piston rod; piston rod 67A in the case of pump 51A and piston rod 67B in the case of pump 51B.

Figure 7:
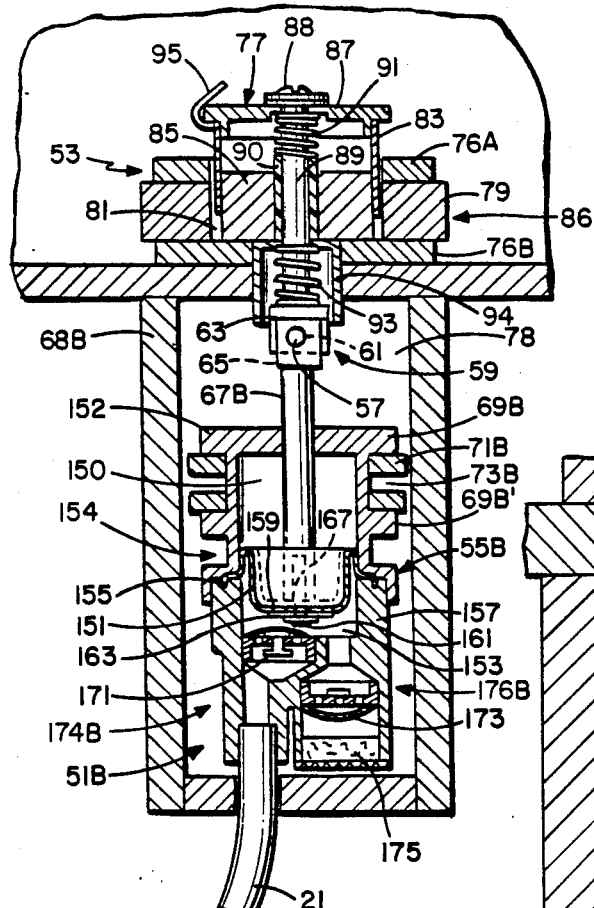
FIG. 7 is a (cut-away) sectional view taken along line 7—7 of FIG. 2, showing the preferred suction pumping chamber and an embodiment of a motor according to the invention.

Referring to FIG. 7, and in particular, the lower portion of the figure, the suction pump 51B is shown. The pump includes a pump body 55B having an upper portion 152 and a lower portion 157 which enclose a cylindrical chamber, which chamber is divided into a upper portion 150 and an lower portion 153 by a diaphragm 151. Diaphragm 151 includes an outer lip 155 which is secured between the two housing portions 152 and 157. The center part of diaphragm 151 is sandwiched between a cup 159 and washer 163 and the assembly is secured to shaft 67B by a screw 161 which screws into a threaded hole 167 in the end of shaft 67B. Inlet umbrella valve 171 and outlet umbrella valve 173 seat in inlet and outlet passageways to chamber 153. Filter 175 seats in the lower portion of the outlet passageway.

Figure 8:
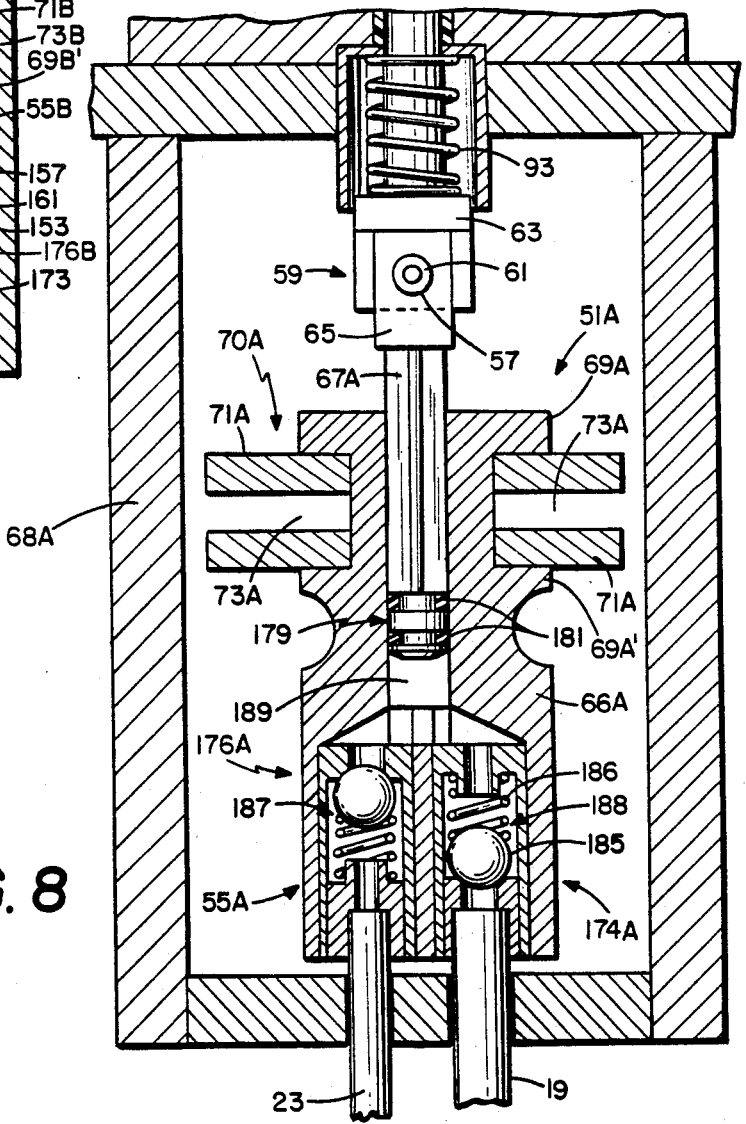
FIG. 8 is a (cut-away) sectional view taken along line 8—8 of FIG. 2, showing the pulsatile lavage/irrigation pumping chamber used in the invention.

Referring to FIG. 8, the PL/IR pump 51A is built somewhat differently than the suction pump because of its different function. The molded pumping housing 66A encloses a cylindrical chamber 189 which is sealed by plunger 179, which is comprised of two O-rings 181 which fit into grooves in the end of shaft 67A. The outlet and inlet valves 187 and 188 respectively are ball valves comprised of resilient balls such as 185 which are normally held in the closed position by springs 186.

Referring to FIG. 6, the apparatus for holding a pump within the housing 11 shall be described in reference to the suction pump 51B. An upper pair of flanges 69B and a lower pair of flanges 69B' extend from the pumping chamber housing 66B. Within suction pump enclosure 68B is a suction pump support 70B which is shaped somewhat like a four-prong tuning fork having prongs 71B. Pump 51B fits into enclosure 68B with flanges 69 passing above the upper pair of prongs 71B and flanges 69B passing below the lower pair of prongs 71B. A backing plate 78 (not shown in FIG. 6) is located so that pump 51B slides up against it when pin 61 has fully entered the hole 57 in flange 65 and flange 65 and 63 engage. Door 74B mounted on enclosure 68B may then be closed. When door 74B is closed, wedges 75B located on door 74B slip in between the prongs 71B forcing them apart and causing them to firmly engage flanges 69B and 69B' on pump 51B, thus holding pump 51B firmly in place. Rod 82B is then pivoted into slot 80B in door 74B and locking nut 84B is screwed inward to secure the door (this is perhaps best seen in FIG. 2). Referring to FIG. 5, pump 51A is likewise secured in enclosure 68A by slipping flanges 69A and 69A' about prongs 71A and, closing door 74A so that wedges 75A force prongs 71A open, slipping rod 82A into slot 80A and screwing nut 84A tight to secure the door.

Referring to FIG. 7, the motor 53, as stated above, is a linear reciprocating motor. It comprises a coil 83 and a core 86. Coil 83 is fixed to reciprocating section 77 of motor 53. Core 86 comprises an outer permanent magnet portion 79 and an inner nonmagnetized but magnetically permeable portion 85. A cylindrical slot 81 is formed within core 86, and coil 83 moves within this slot. Magnetically permeable steel plates 76A and 76B sandwich the permanent magnet, and also may be considered as part of the motor core. Coil 83 is mounted on a circular support 87 which is attached to shaft 89 by screw 88. A hollow cylindrical bearing 90 fits into a cylindrical bore in core 86 and shaft 89 slides within bearing 90. Helical coil spring 91 is located on shaft 89 with the axis of the spring corresponding to the axis of the shaft, and with one end of the spring seating against support 87 and the other end of the spring seated against bushing 90. Similiarly the coil spring 93 fits coaxially about the bottom of the shaft 89 and seats between the top of flange 63 and a spring enclosure 94 which forms an integral part of bushing 90. It is noted that the springs 91 and 93 will function properly as long as one end is seated against a portion of the motor that is moveable with the coil while the other end is seated against a portion of the motor which is fixed to the core. Thus, in the context of providing a seat for the spring, bushing 90 may in this embodiment be considered to be part of the motor core. Coil 83 is electrically connected to circuitry in the housing by means of braided wires 95.

Figure 12:
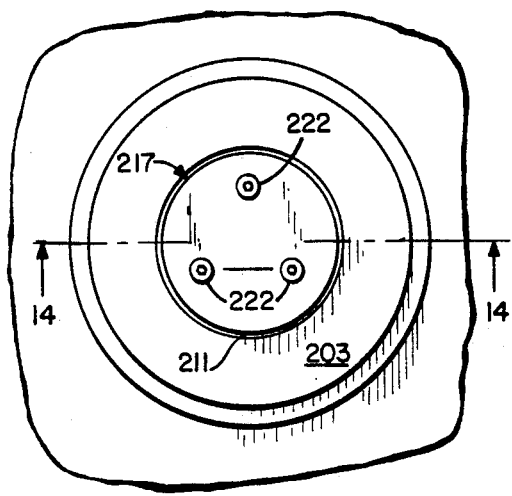
FIG. 12 is a top view of the preferred linear reciprocating motor according to the invention.
Figure 13:
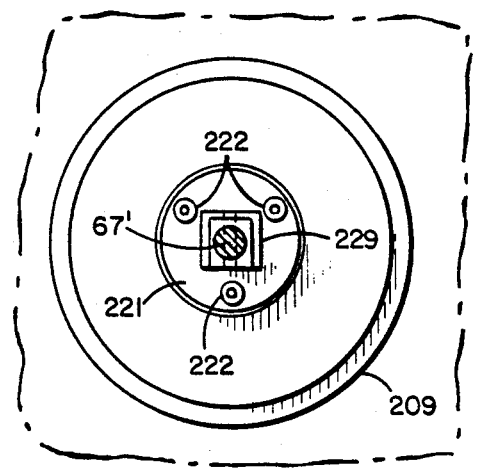
FIG. 13 is a bottom view of the motor of FIG. 12.
Figure 14:
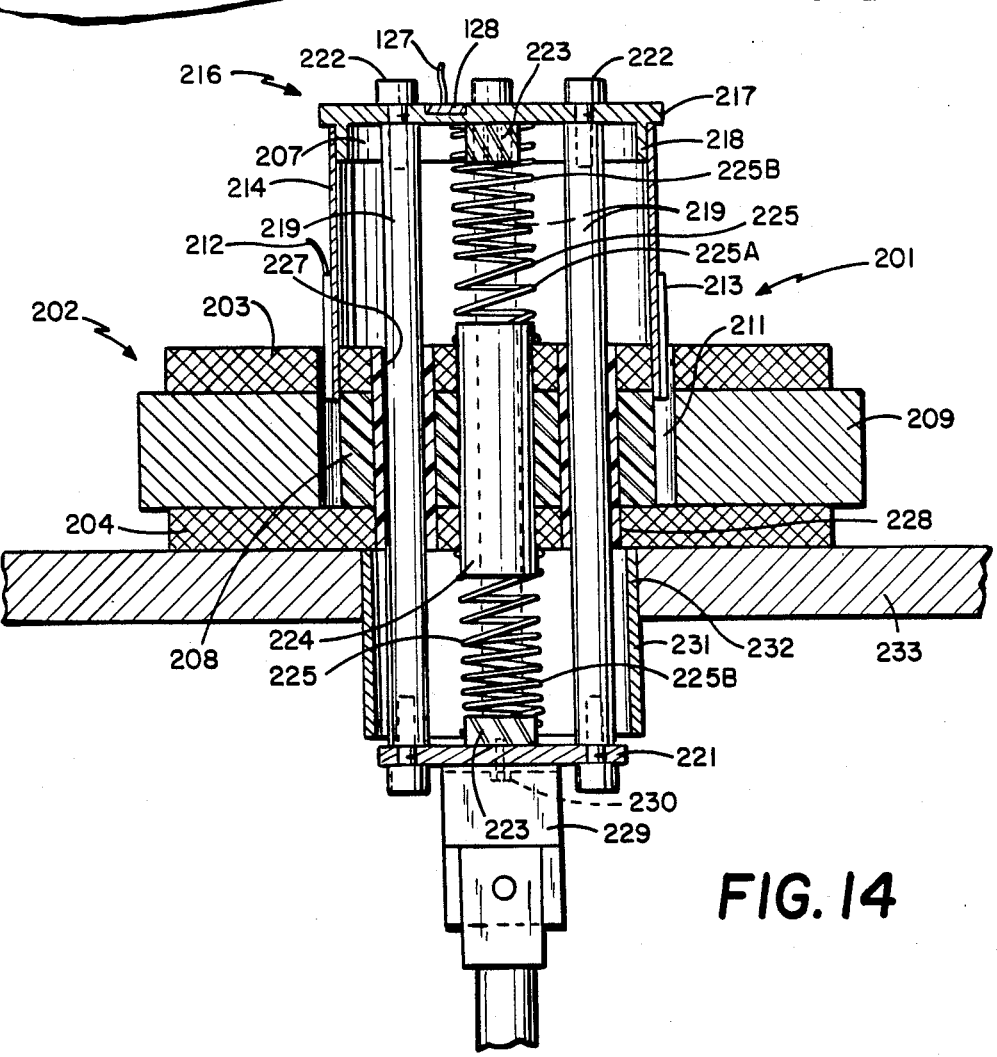
FIG. 14 is a cross-sectional view of the motor of FIG. 12, taken along lines 14—14.

Referring to FIGS. 12, 13, and 14 an alternative embodiment of the linear motor is shown. This embodiment is presently the preferred embodiment. A top view of the motor is shown in FIG. 12, a bottom view in FIG. 13, and a cross-sectional view in FIG. 14. Motor 201 comprises a core 202 and a moving coil 213. Core 202 includes a magnetically permeable top plate 203, a magnetically permeable bottom plate 204, an inner magnetically permeable core 208 and a permanent magnet 209. Coil 213 moves in a cylindrical slot 211 between magnet 209 and inner core 208. Coil 213 is attached to a cylindrical coil support 214 which in turn is attached to a ring-shaped flange 218 on top disc-shaped support 217. Top support 217 is secured to a disc-shaped bottom support 221 by three shafts 219 by means of screws such as 222. Shafts 219 are moveable in bearings 227 which seat in cylindrical bores 228 through core 202. Coil springs 225 seat between the core 202 and supports 217 and 221. Spring alignment bosses 223 are attached to the center of supports 217 and 221 and spring alignment post 224 seats in a cylindrical bore through the center of core 202. One end of the spring 225 fits around the bosses 223 and the other end fits around the post 224 to maintain the spring in alignment. Springs 225 are helical coil springs with variable coil spacing; that is, the coil spacing at one portion 225A of each spring 225 is different than the coil spacing at another portion 225B of the same spring 225. The motor is attached to flange 229 by screw 230, and the rest of the attachment to the pump is as described above. The motor 201 sits in a cylindrical hole 232 in pump housing 233. A thermistor, such as 128, is encapsulated in epoxy and bolted to the support 217 and is connected to the electronic circuitry, which shall be described below, by braided wires 127. Coil 213 is connected to the electronic circuitry by braided wires 212.

Figure 9:
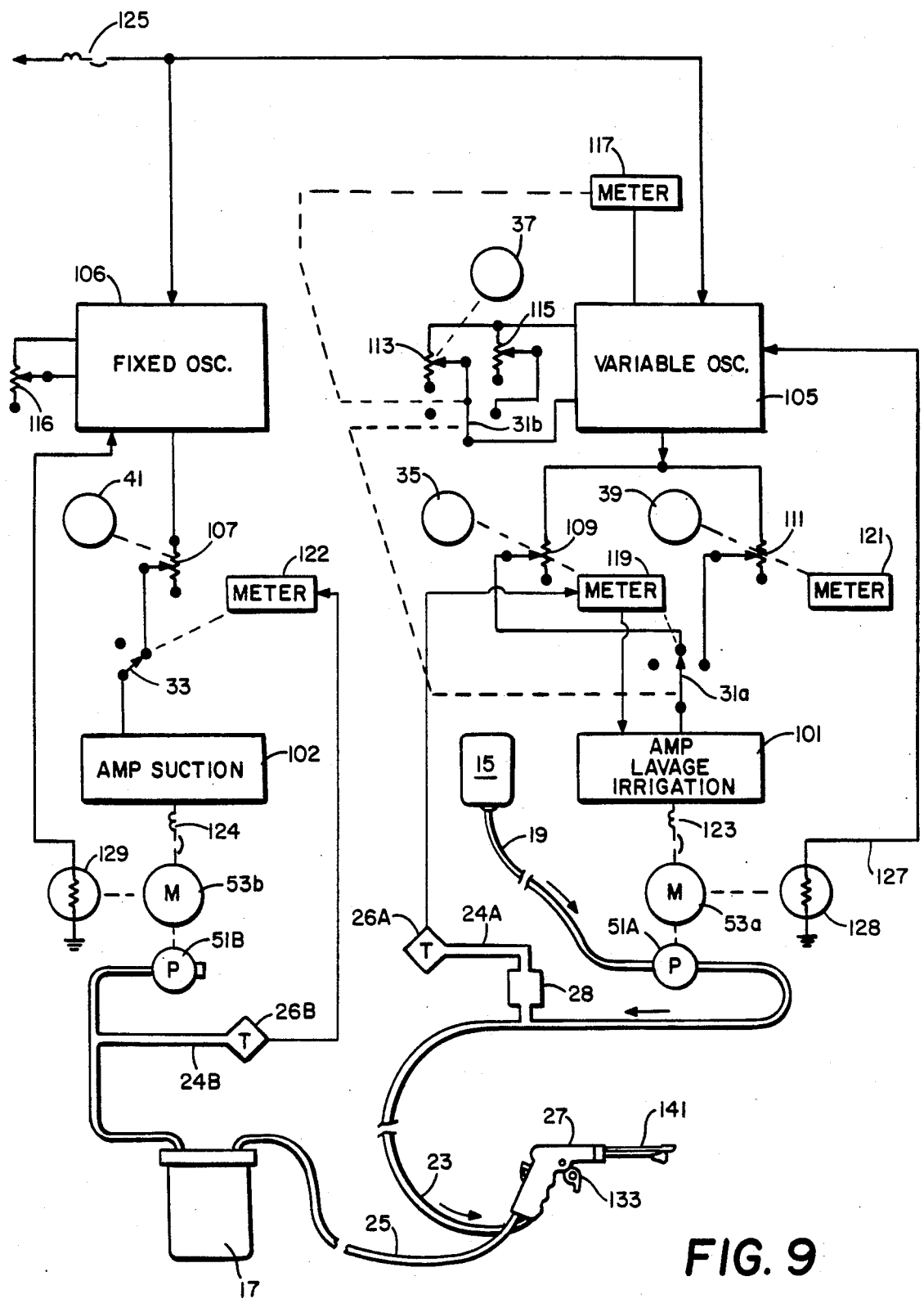
FIG. 9 is a block diagram showing the operation of the controls and various functions of the preferred embodiment of the invention.

Referring to FIG. 9, a discussion of the electrical circuitry in terms of a functional diagram will be given before proceeding to the detailed discussion of the circuitry, in order to make that discussion more clear. In FIG. 9 the physical connection between pump 51A and motor 53a and pump 51B and motor 53b is shown by a dotted line. Power for the motors 53a and 53b is supplied by signals provided by amps 101 and 102 respectively which is supplied to the motors through circuit breakers 123 and 124 respectively. Oscillating signals which are amplified by amplifiers 101 and 102 are provided by oscillators 105 and 106 respectively. Power to the oscillators is provided through circuit breaker 125.

The switches in FIG. 9 correspond to the switches in FIG. 3. These switches are actually double pole switches. The two poles of switch 31 are shown separately at 31a and 31b in FIG. 9 for clarity. The dotted line indicates that the two switches move together.

As can be seen in FIG. 9, switch 33 has a closed position in which it connects the fixed oscillator 106 to the suction amplifier 102, which is the suction "on" position, and an open circuit position which is the suction "off" position. In the "on" position switch 33 also activates meter 122 to read the vacuum from the suction transducer 26B. This is shown by the dotted line. Meter 122 could also be connected to read the power going through variable resistor 107, or the power off the amplifier 102, both of which would give a meaningful output to the meter.

The far left position of switches 31a and 31b is an open circuit "off" position. In the central position switch 31a connects variable resistor 109, which is controlled by knob 35, into the circuit between oscillator 105 and amp 101. Variable resistor 109 controls the amplitude of the signal to amplifier 101 and thus controls the power output of the amplifier and ultimately of the pump. Since the power output of the pump is directly related to either the rate of flow or the pressure, meter 119 can be calibrated in either percent of power units, pressure units, or rate of flow units. In the embodiment described, it is chosen to calibrate the meter in pressure units, and the pressure is read off pressure transducer 26A by meter 119 when switch 31a is in the central position. The pressure units chosen are pounds per square inch. Of course, any other pressure units, such as millimeters of mercury could also be chosen. In the central position, switch 31b connects variable resistance 113 into the variable oscillator 105 circuitry. Variable resistance 113 is controlled by knob 37, the pulsatile lavage frequency control, to control the frequency of variable oscillator 105. In the central position switch 31b also connects meter 117 to the circuitry of variable oscillator 105. In this position of switch 31b meter 117 displays the frequency of oscillation of the variable oscillator 105. In the far right position switch 31a connects variable resistance 111 between oscillator 105 and amplifier 101. Variable resistance 111 is controlled by knob 39 which, as can be seen from FIG. 3, is the irrigation power control. Meter 121 displays the output of variable resistance 111. Again this output can be calibrated in either pressure units, rate of flow units, or a power unit. In the present embodiment it is chosen to calibrate it in percent of flow. In the far right position, switch 31b connects variable resistor 115 into the electrical circuit of variable oscillator 105. Variable resistance 115 is not controlled by an external knob, but rather is controlled by a "behind the set" control which determines the "fixed" frequency of the irrigation mode. Generally this resistance is set so that a high oscillation frequency, i.e. in the range between 30 and 40 cycles per second is chosen since a high frequency provides a nearly continuous flow. In the embodiment shown switch 31b when switched to the far right position deactivates the meter 117, although one obviously could choose to leave the meter connected in this situation if one desired to read out the "fixed" frequency.

The oscillation frequency of fixed oscillator 106 is determined by variable resistance 116, which is also a "behind the set" control. The setting of variable resistance 116 determines the frequency of the suction motor and pump.

Also shown in FIG. 9 are thermistors 128 and 129 which are physically attached to motors 53a and 53b as shown by the dotted lines. Thermistors 128 and 129 are temperature sensitive resistors which in a voltage divider circuit will vary the voltage output of the circuit proportionally to the temperature of the motor. As the temperature of the motor increases the internal resistance of the moving coil increases which reduces the effective power produced by the motor. The output of the voltage divider circuit incorporating thermistors 128 and 129 is fed into the circuitry of the oscillators 105 and 106 respectively. The circuitry is arranged so that this output causes the power input to the oscillators 105 and 106 respectively, and therefore the power level of the oscillater output signal, to increase precisely as needed to account for the variation of performance of motors 53a and 53b respectively with temperature.

FIG. 9 also shows a connection between pressure transducer 26A and amplifier 101 through meter 119. By means of this connection, the circuitry causes the amplifier 101 to shut down if the pressure in line 23 rises above a certain predetermined pressure, and to turn back on when the pressure drops below that predetermined pressure. This circuitry causes motor 53a and pump 51A to shut down whenever valve 133 on the lavage handpiece (FIG. 4) is closed, and to resume operation when the valve 133 is opened.

Figure 10A:
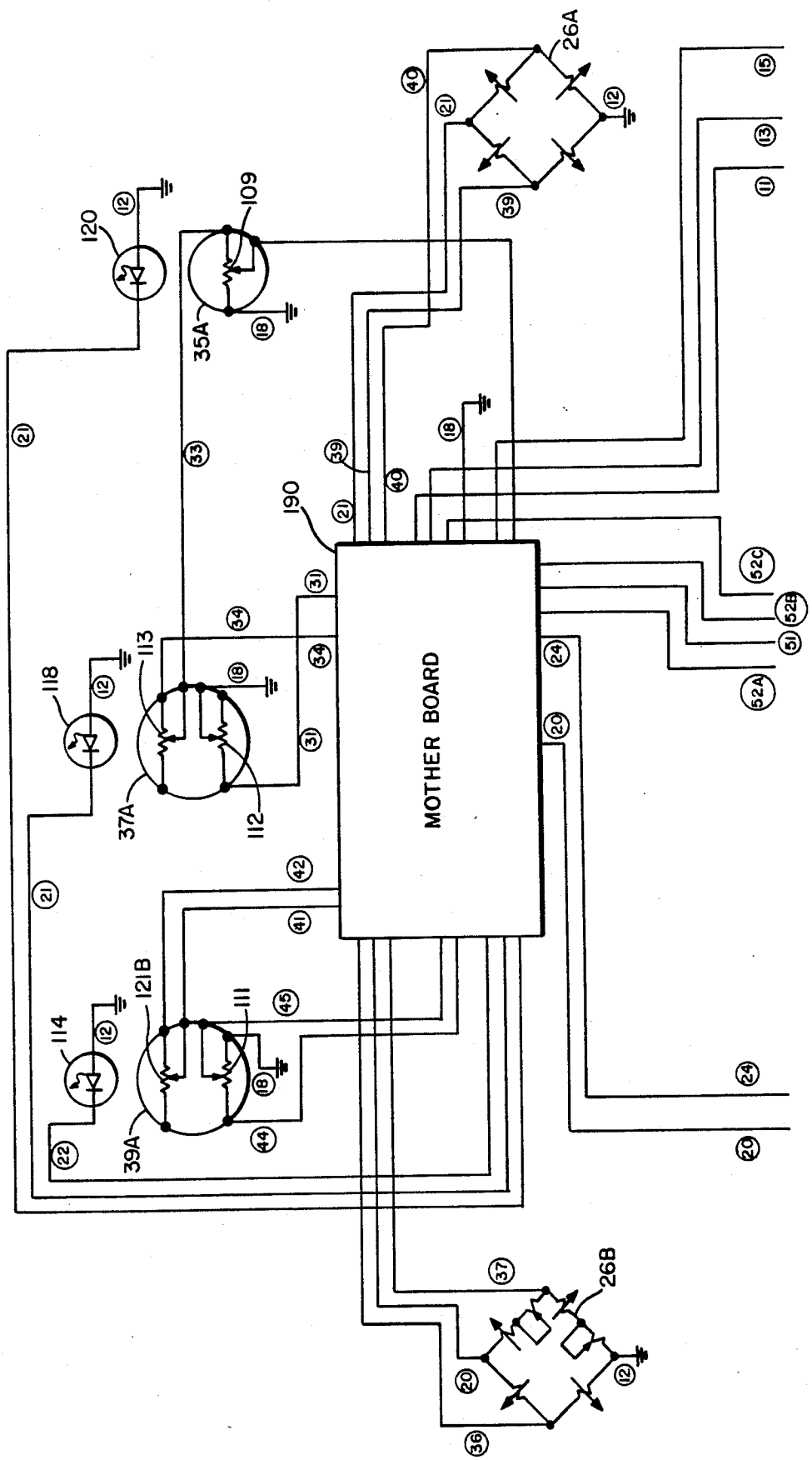
FIG. 10A is the upper half and FIG. 10B is the lower half of a schematic diagram of the electronics according to the preferred embodiment of the invention.
Figure 10B:
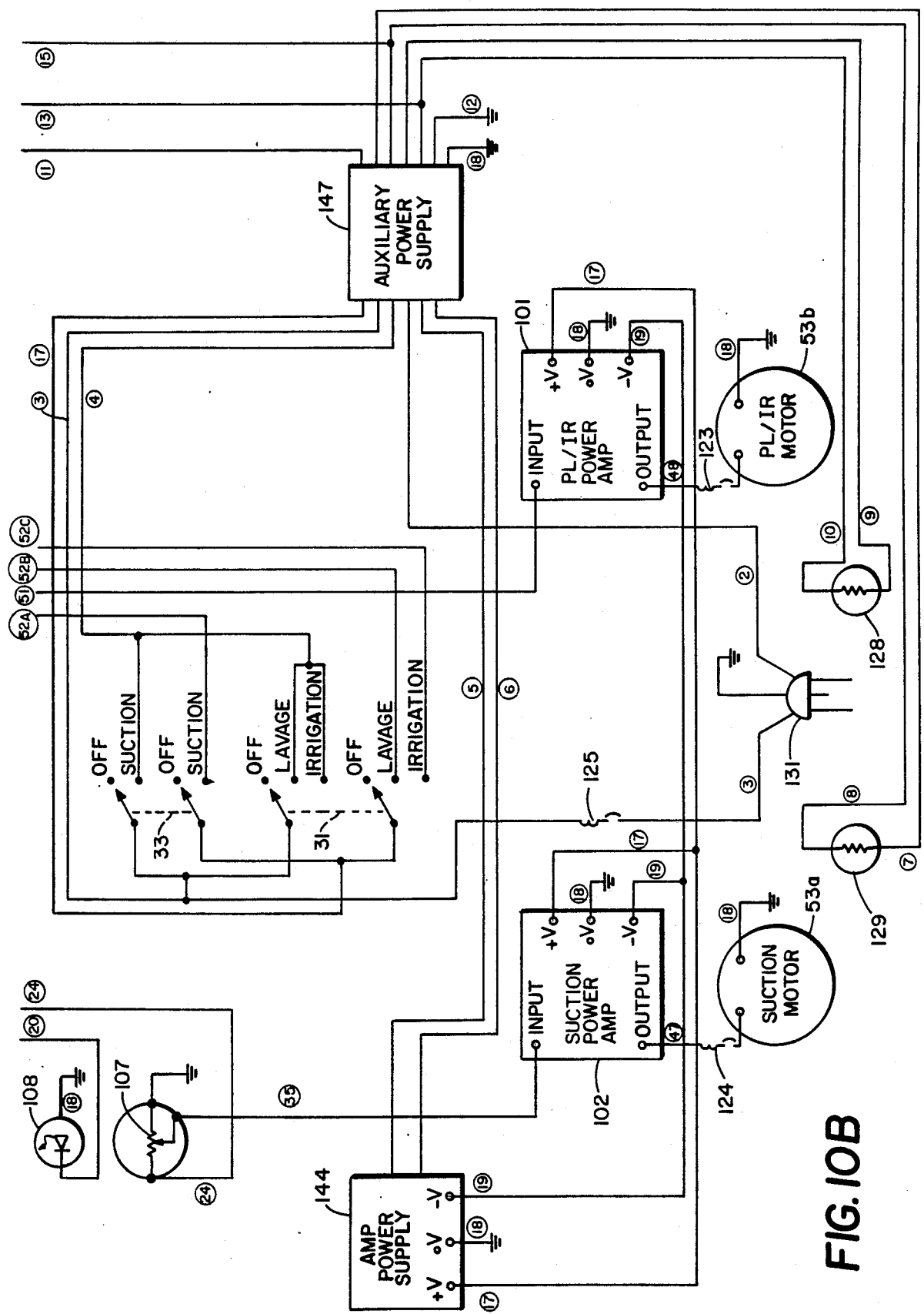

Turning now to a more detailed description of the electronic circuitry, the electrical interconnections of the various electronic components is shown in FIGS. 10A and 10B. If FIG. 10A is placed above FIG. 10B, so that the wires leaving FIG. 10A at the bottom of the page overlap the wires entering FIG. 10B at the top of the page, a complete electrical schematic of the electronic portion of the invention is obtained. The numbers contained in small circles in FIG. 10A and 10B label the individual wires, and thus enable the wires to be traced from one page of the drawing to the next. Note that some wires carry identical numbers, for example ㉑ and ⑱. This is an indication that these wires connect at some point, usually on the Motherboard. Beginning at the top of FIG. 10A and proceeding to the bottom of FIG. 10B, the components of the electrical circuit include light emitting diodes (LED) 114, 118, and 120 which are illuminated as appropriate to show that the irrigation function, the pulsatile lavage frequency control function, and the pulsatile lavage pressure control function respectively are operating (see FIG. 3). Beneath these diodes are two dual variable resistor potentiometers 37A and 39A and a single potentiometer 35A which contain the variable resistors 109, 111, and 113, which function as described above in connection with FIG. 9. Potentiometers 35A, 37A, and 39A are controlled by knobs 35, 37, and 39 respectively (see FIGS. 3 and 9). Variable resistor 121B in dual pot 39A is part of the circuit regulating irrigation meter 121 to provide the proper meter output. Variable resistor 112 in dual pot 37A provides an adjustment to the gain of amplifier 101 to keep the amplifier output flat as the frequency changes. Beneath the dual pots are the irrigation/lavage transducer 26A and the suction transducer 26B, also described in FIG. 9, and the Motherboard 190. Motherboard 190 is hybrid circuit which provides for most of the connections between the various electrical components, and which shall be described below in connection with FIGS. 11A through 11L. At the top left of FIG. 10B is suction LED 108 (See FIG. 3) and the suction amplifier potentiometer 107 which functions as described in reference to FIG. 9. Switches 31 and 33 connect power socket 131 with the power supplies and the Motherboard through circuit breaker 125. The amplifier power supply 144 supplies power to the amplifiers 101 and 102, while the auxiliary power supply 147 supplies power to the other components in the circuit. Amplifier 101 is connected to PL/IR motor 53a through circuit breaker 123 while amplifier 102 is connected to suction motor 53b through circuit breaker 124 as discussed in reference to FIG. 9. The thermistors 128 and 129, which are mounted on the PL/IR motor 53a and the suction motor 53b respectively, are connected with the auxiliary power supply and the Motherboard as indicated.

Figure 11A:
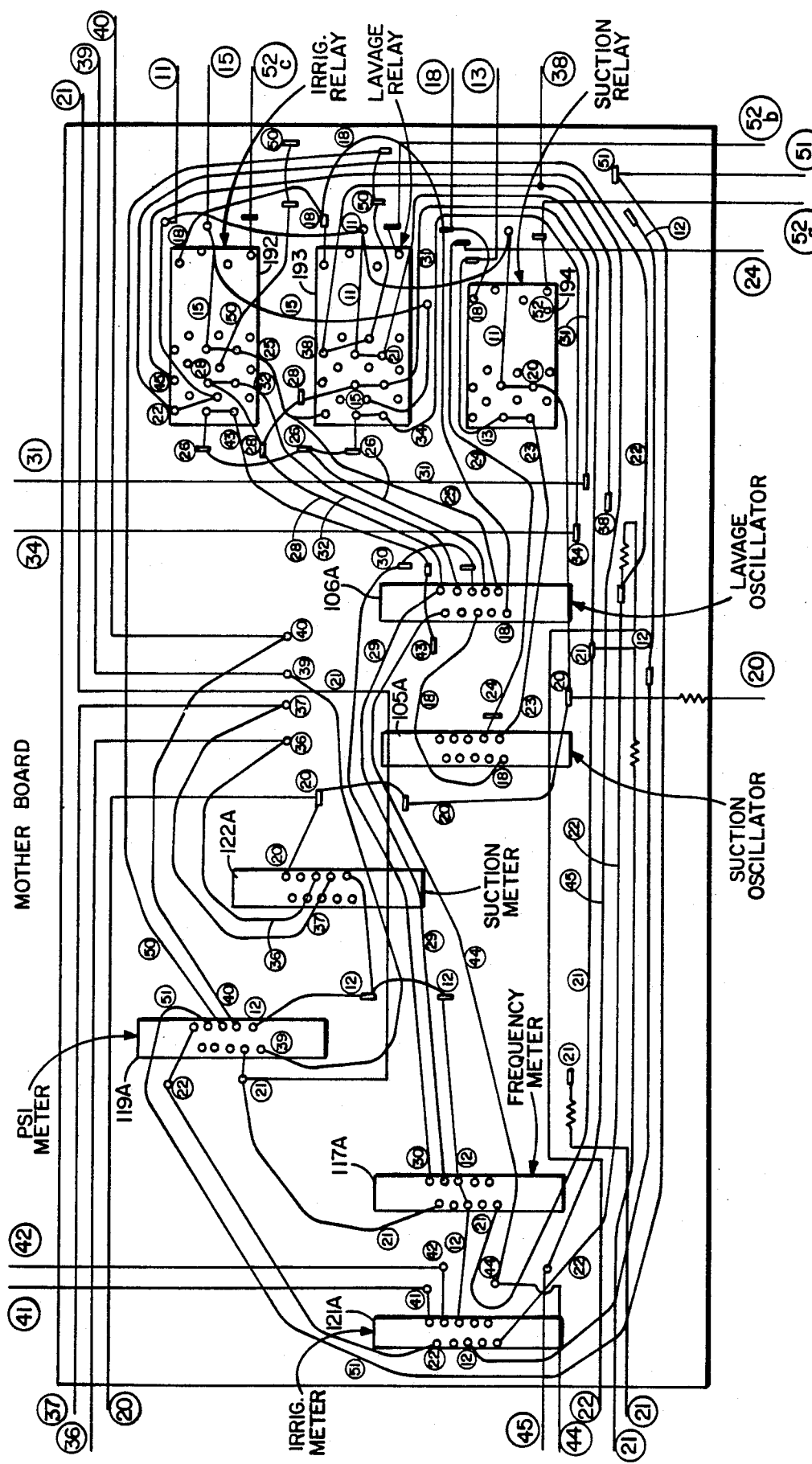
Figure 11B:
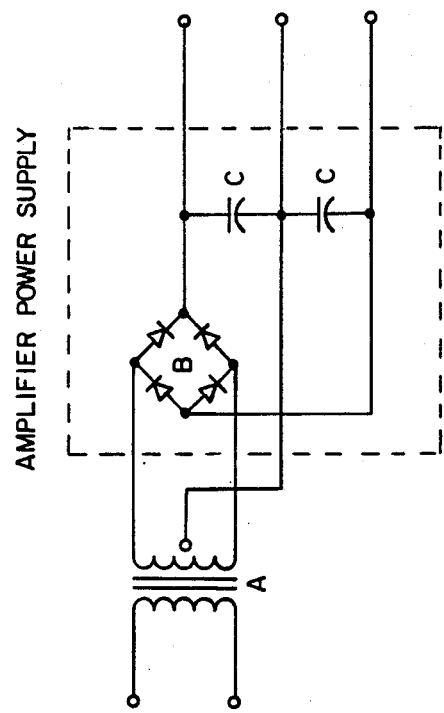
Figure 11C:
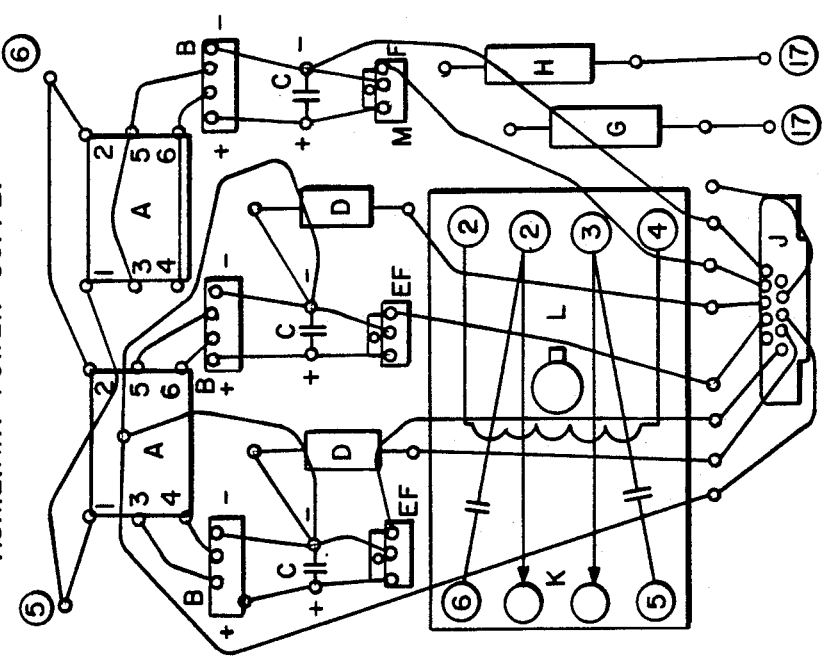
Figure 11D:
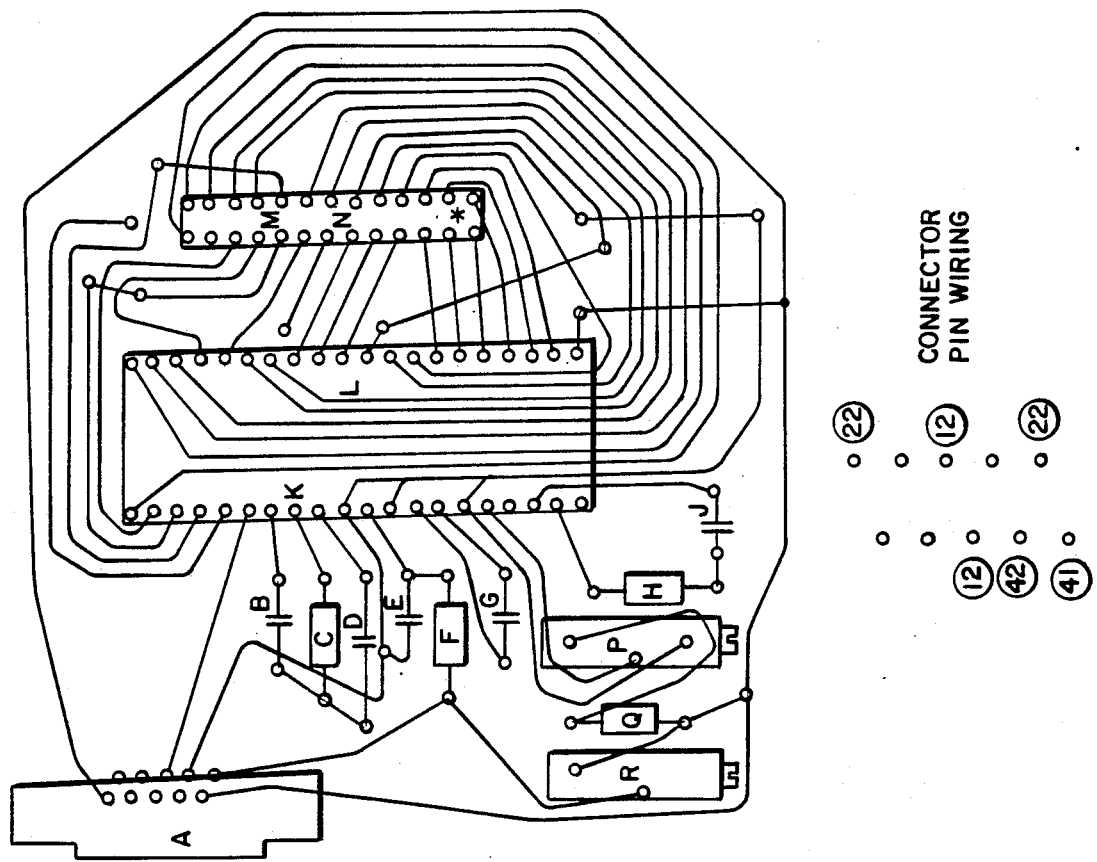
Figure 11E:
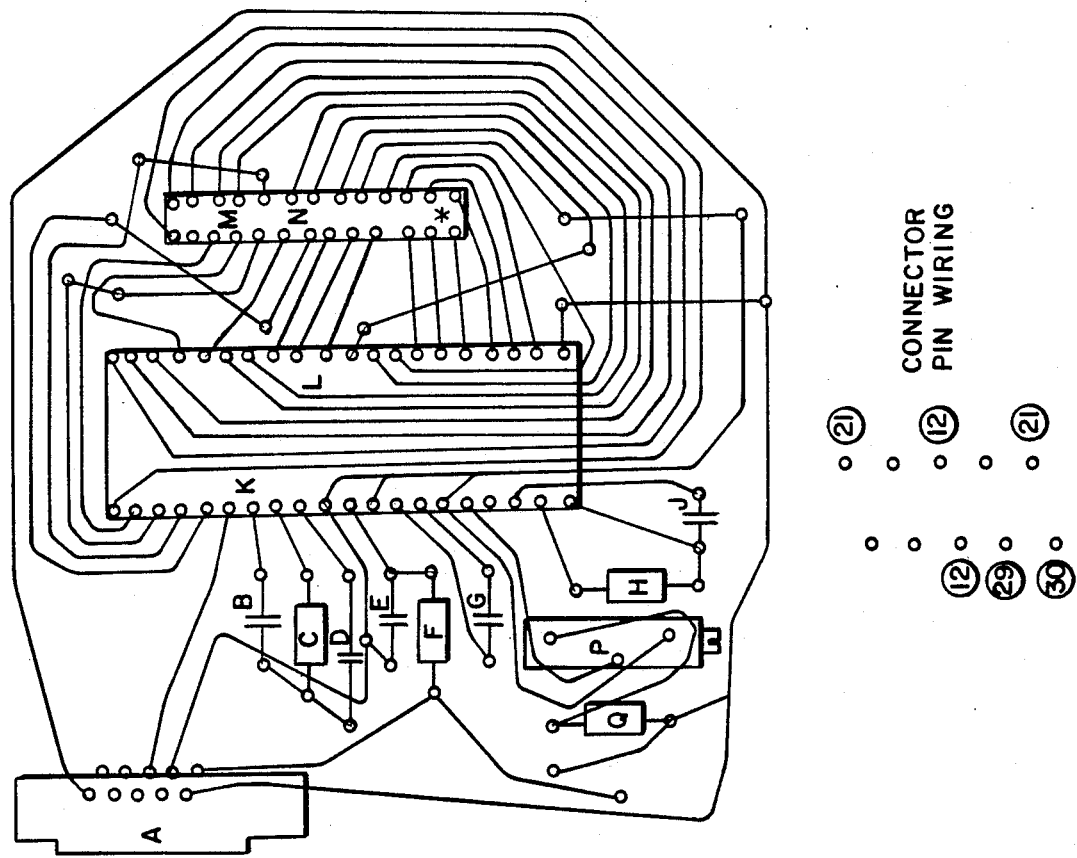
Figure 11F:
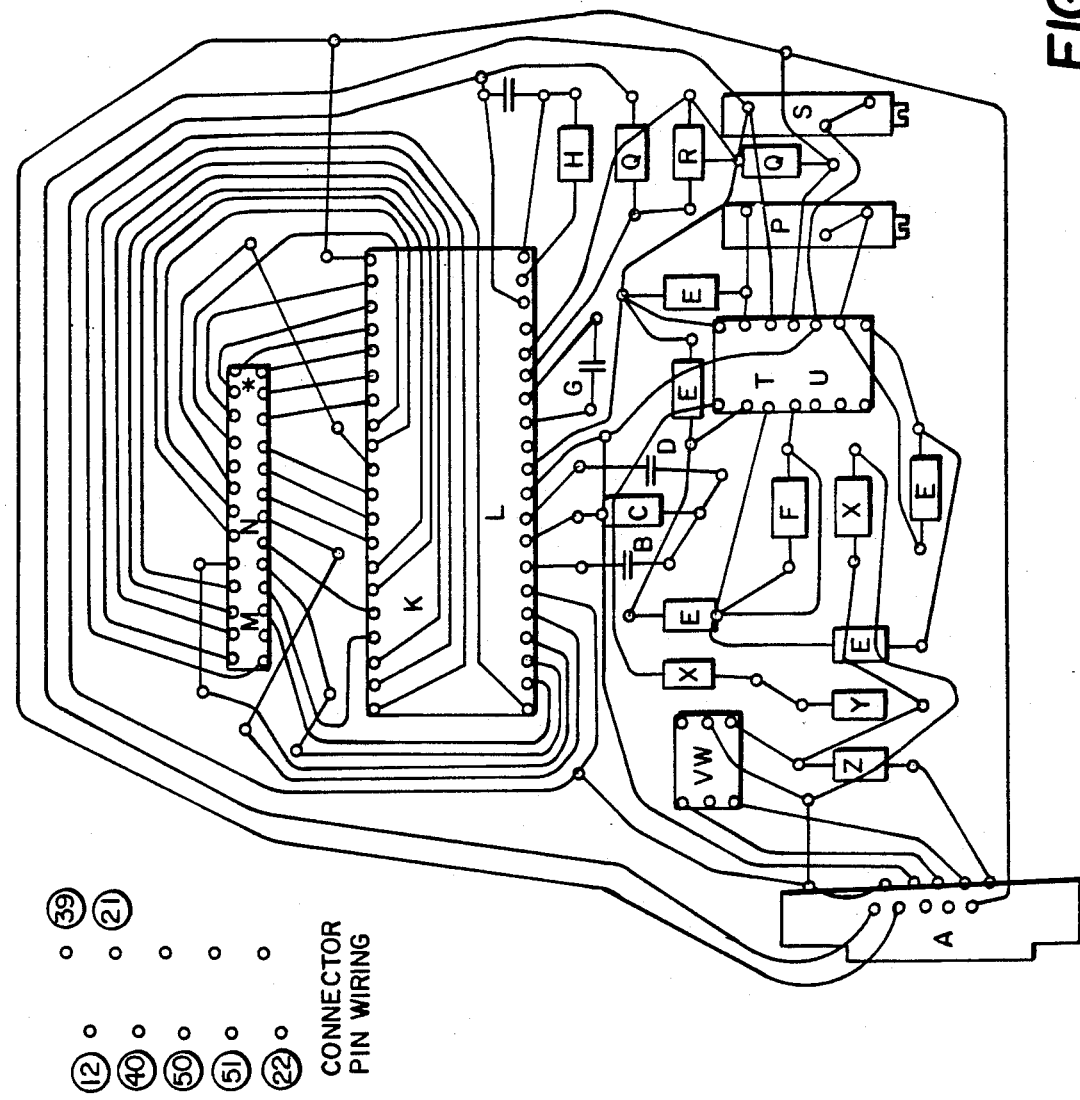
Figure 11G:
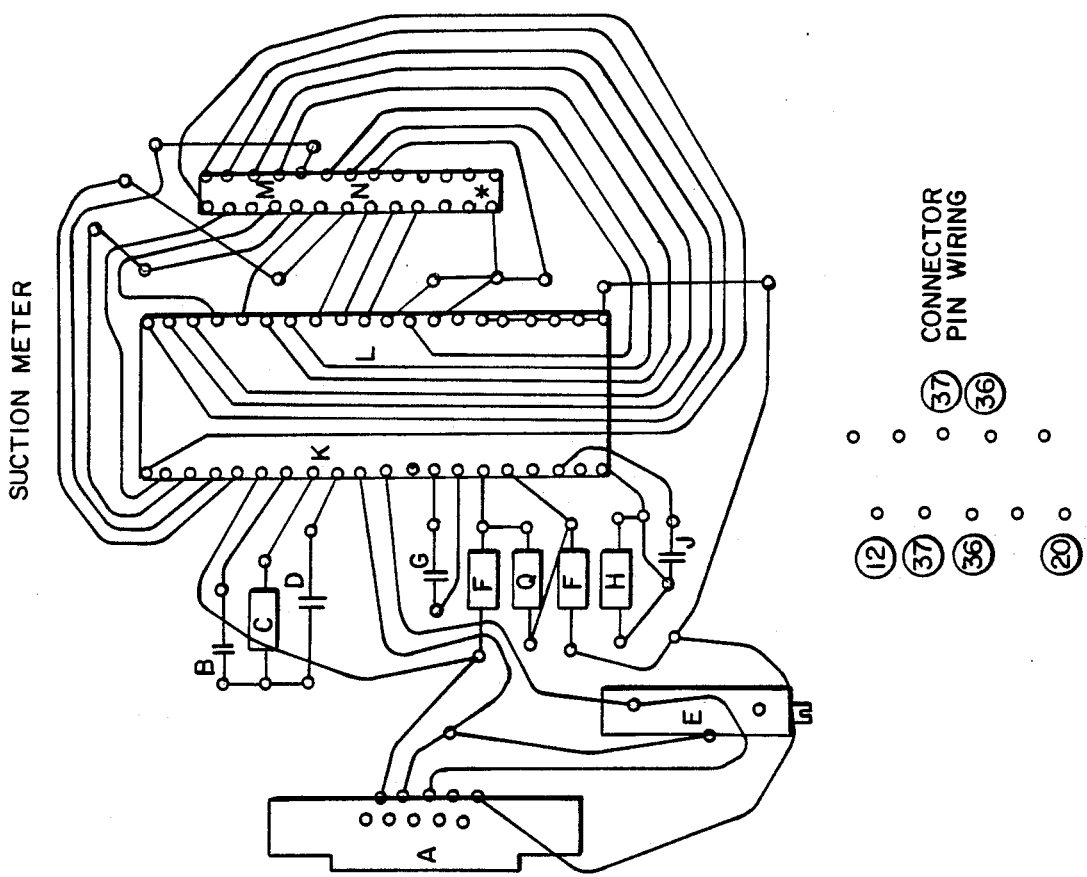
Figure 11H:
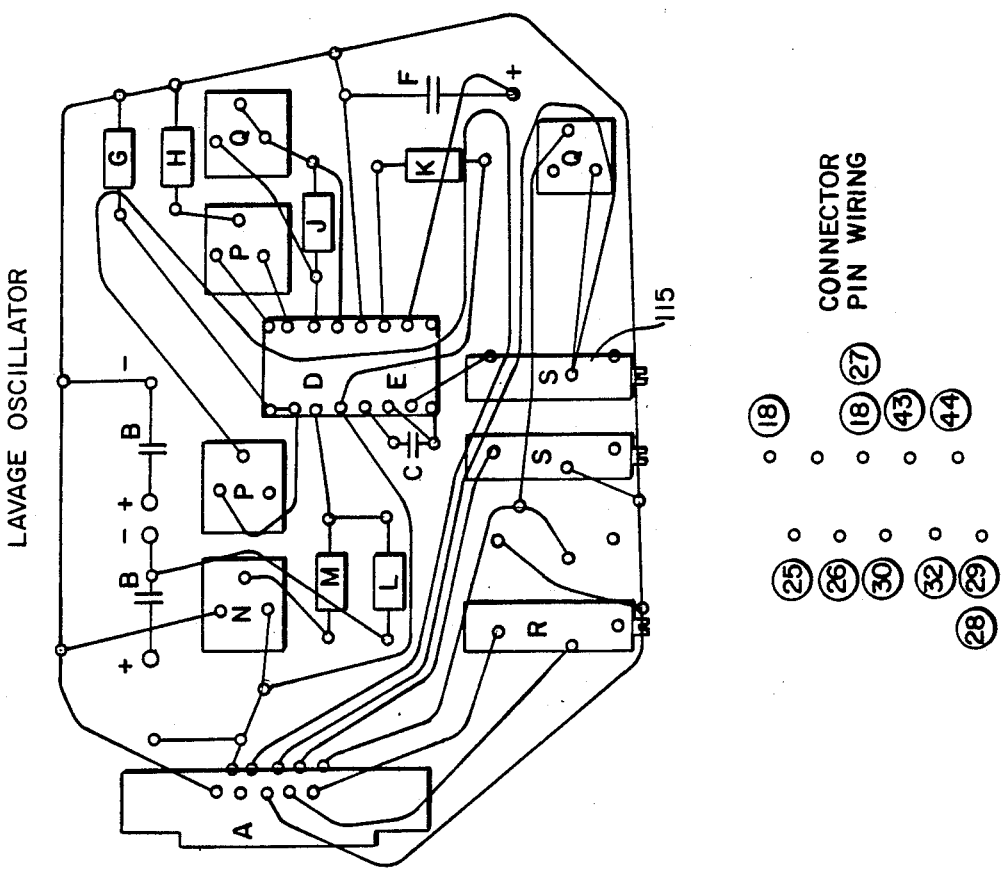
Figure 111:
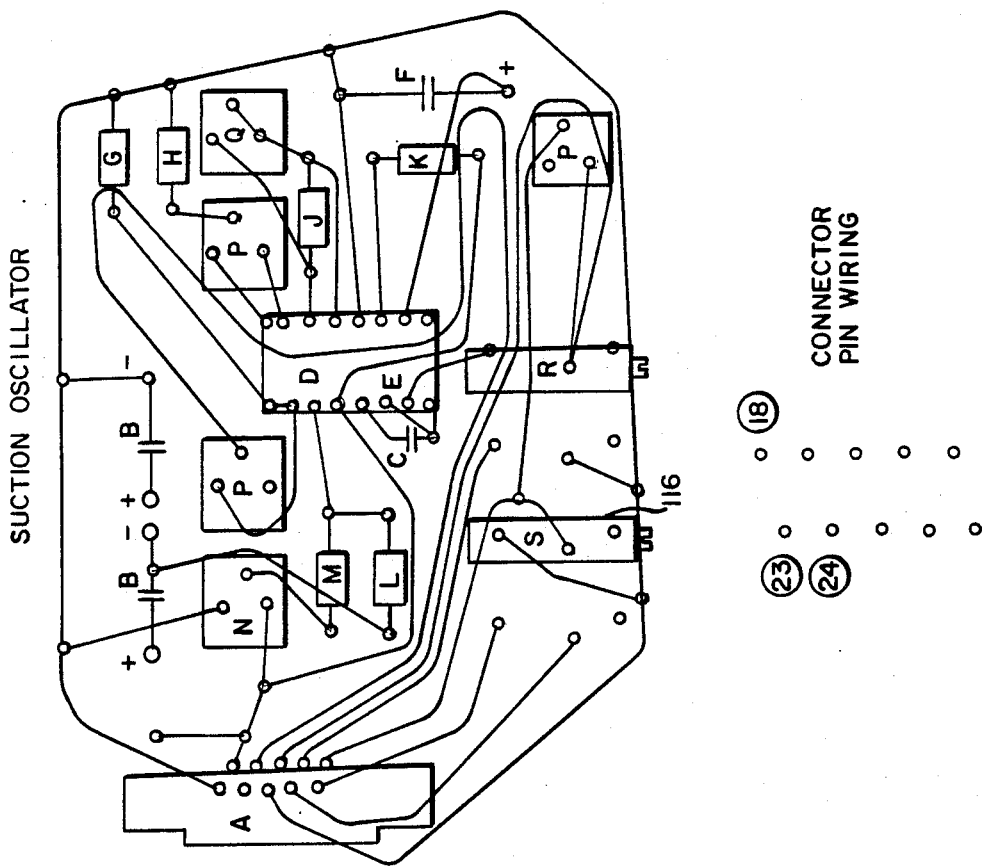

The Motherboard layout is shown in FIG. 11A. The Motherboard includes six subsidiary boards: irrigation meter board 121A, frequency meter board 117A, PSI meter board 119A, suction meter board 122A, lavage oscillator board 105A, and suction oscillator board 106A (see also FIG. 9). The details of each of these boards is given in a subsequent figure. The Motherboard also includes three relays, the irrigation relay 192, the lavage relay 193, and the suction relay 194. The numbered wires shown coming into the Motherboard from outside the figure are the numbered wires entering the Motherboard in FIG. 10A and connecting to the various components shown in FIGS. 10A and 10B. Each of these connections can easily be traced from figure to figure using the numbered wires. The wires connecting the various components on the Motherboard are also labeled with numbers within circles. These wires will be indicated on the detailed drawings of the component boards so that the interconnections will be clear. The ten heavy dots on each of the subsidiary boards are connector pins of WTB10PR7JTA connectors on each of the boards. The pin wiring to these connectors is shown in detail on the subsequent figures. The connections between the subboards and the relays can easily be traced on the Motherboard using the numbered wires, and thus they shall not be discussed further.

The detailed electrical components and connections between the components for the amplifier power supply 144, the auxiliary power supply 147, the irrigation meter board 121A, the frequency meter board 117A, the PSI meter board 119A, the suction meter board 122A, the lavage/irrigation oscillator board 105A, the suction oscillator board 106A, and the suction transducer 26B, are shown in FIGS. 11B through 11I and 11L respectively. Each of these amplifiers, meters, oscillators and transducers are devices that are well understood in the electrical art, which one skilled in the art can build once their function has been described. Instructions on the detailed connections, can usually be obtained with the purchase of the principal parts, and/or will generally be understood from the electrical literature. However, for completeness, each of the individual components is labeled and indicated on the drawings and each of the connections between the components are shown. In each of the drawings the circled numbers represent connections to wires coming into or located on the Motherboard. In each of the drawings which incorporates a WTB10PR7JTA connector, the wiring to the cable connector which presses into the WTB10PR7JTA connector is shown on the drawing. The wiring is shown as it would appear if one turned the cable connector so that the pins are visible and looked down at the pins, since this is the manner in which the cable connector is ordinarily viewed. In each of the drawings the position of the cable locator is shown by a star. The pressure feed back loop which is shown by the connection between transducer 26A and amplifier 101 in FIG. 9 is located on the PSI meter board (FIG. 11F) and consists of the ECG987 quad operational amplifier and the ECG3047 triac opto coupler. These are off-the-shelf items, and instructions for use of the items to produce a feed-back loop may be obtained with purchase of the items. The connections to produce the feed-back loop are, of course, also shown in FIG. 11F. The "behind the set" variable resistor 115 for setting the "fixed" irrigation frequency (see discussion of FIG. 9 above) is indicated on FIG. 11H, while the variable resistor 116 for setting the frequency of the fixed or suction oscillator 106 is indicated on FIG. 11I. It may be noticed that while the suction oscillator board (FIG. 11I) shows wires to nine sockets on the connector A, the connector pin wiring on the same figure shows connections to only three pins. This is due to the fact that the suction and lavage oscillator boards are wired the same for manufacturing convenience, but only three of the pins need to be connected to the Motherboard 190 for the suction oscillator to function properly.

Each of the meter boards shown in FIGS. 11B through 11G is connected to a liquid crystal display (LCD) to produce the visible meter readings as shown for example on meters 117 and 119 in FIG. 3. The connections between each of the meter boards and its LCD display are identical and are shown in FIGS. 11J1, 11J2, 11K1, 11K2, and 11K3. FIG. 10J1 shows the connection between the component side of the meter board and the back of the LCD board. The connection is made between the 26 pin header 196A (labeled M on each of the meter boards) and a corresponding 26 pin header 196B on the LCD board by means of 26 line cable 197. The location of the 1CL7106CH chip is shown at 198 on the meter board in order to more clearly define the location of the header 196A. The front of the LCD board is shown in FIG. 10J2 and consists of LCD chip 199 mounted on a 40 pin chain terminal 195. The connections between the 26 pin header 196B and the back of the chain terminal 195 are shown in FIG. 10K1. There are also etched connections between the white dots such as 200 (FIGS. 10K2 and 10K3) on the back of the LCD chip. These connections are the same for the power, frequency, and psi LCD 199B and are shown in FIG. 10K3. The connections are slightly different for the suction LCD 199A and are shown in FIG. 10K2.

Figure 11L:
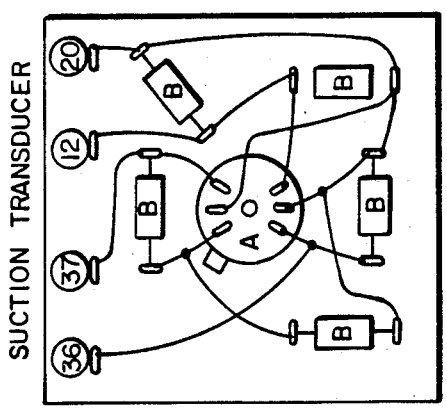

Most of the electrical parts to produce the circuits described above are common parts, the identity of which unambiguously disclosed by the labels on the figures. The connectors such as the WTB10PR7JTA are made by Airborn, Inc. of Addison, Tex. 75001. The Stancor PPC-3 power transformer may be purchased from Newark Electronics at 1225 North Main, North Canton, Ohio. The suction power amp is an English amplifier designated ILP Y-200 and may be purchased from Gladstone Electronics, 901 Fuhrman Boulevard, Buffalo, N.Y. The Foxboro 1800 transducer and the balance resistors which form part of the suction transducer and are shown in FIG. 11L may be obtained from Foxboro/ICT at 1750 Junction Avenue, San Jose, Calif. The PL/IR transducer is an off-the-shelf Foxboro 703 transducer. The suction and PL/IR thermistors 129 and 128 are Oneida GB 1224 thermisistors and may be purchased from Oneida at Box 678 Road 2, Baldwin Extension, Meadville, Pa. 16335. All other parts may be purchased from an electronics distributor such as Canico, Inc. 1355 Shoreway Road, Belmont, Calif. 94002.

The materials from which the various parts of the invention are made are for the most part evident from the functions; we shall briefly review the preferred materials, although it should be understood that many other suitable materials could be used. The PL/IR fluid supply container 15 is formulated out of vinyl plastic as are the various fluid tubes such as 19, 21, 23, and 25. Handpiece 27 is molded out of ABS plastic, and drainage tank 17 is formed from an acrylic plastic. Stand 13 is made of chrome plated steel, and housing 11 is formed of fiberglass. The various threaded screws and rods such as 82A (FIG. 2) are made out of stainless steel while the knurled knobs such as 84A are made of aluminum. The pump bodies, such as 55A, are molded of acrylic resin but ABS plastic, stryene plastic or rigid vinyl would be suitable. Diaphragm 151 is made of soft vinyl, but KRATON TM elastomer or rubber are also suitable. The valves 171 and 173 may be made out of similar materials, although presently KRATON elastomer is used. The pump shafts 67B as well as the flanges such as 65 and 63 are made of acrylic resin, although ABS plastic or styrene are also suitable. In the PL/IR pump (FIG. 8) ball valves 185 is made of ethylene propylene while the springs 186 are made of stainless steel. O-rings 181 are made of soft vinyl, KRATON, or rubber. Filter 175 is made of cotton or foam plastic. The materials of the motor parts shall be discussed in terms of the preferred embodiment of FIG. 14; materials of the embodiment of FIG. 7 will be clear by analogy. The moving coil 213 can be purchased already mounted on cylinder 214 from a source of acoustic speaker parts, such as Quam Nichols, Marquette Road and Prairie Avenue, Chicago, Ill. 60637. Cylinder 214 to which the coil is attached is a piece of thin (about 0.005 in.) aluminum. Supports 217 and 221 are made of aluminum, and cylinder 214 is attached to support 217 by an epoxy adhesive, such as 3M TM brand No. 2214 regular. Shafts 219 are made of aluminum while bushings 227, bosses 223, and post 224 are made of TEFLON TM polytetrafluoroethylene. Spring 225 and the various screws such 222 are made of stainless steel. Magnet 209 is a ceramic magnet and plates 203 and 204 are made of any permeable steel. Housing parts 231 and 233 are preferably made of aluminum for heat dissipation purposes, but also may be made of fiberglass, ABS plastic, etc. as desired. Braided wire 127, 212, and 95 is a rope-like fabric that is impregnated with a conductive metal such as #P-1603 lead wire available from The Montgomery Company, Canal Bank, Windsor Locks, Conn. 06096.

Turning now to the operation of the system, if the intended use is to be in surgery or other use where sterile or very clean conditions are necessary, all parts of the system that contact the lavage fluid will likely have been removed after the last use, and thus these parts will have to be attached. These parts include the fluid supply bag 15, lines 19,24A, 24B, 21, 23 and 25, drainage bag 18, couplings 24C and 24D, filter 28, T's 22A and 22B, lavage handpiece 27, and pumps 51A and 51B. All these parts are made out of cheap materials, and all, except perhaps the drainage bag 18, are resterilizable, and thus either a new set of these parts or a set that has been resterilized may be used. The pumps are inserted as shown by the dotted lines in FIG. 6 and the door 74B is closed forcing wedges 75B between prongs 71B causing them to separate and grip flanges 69B and 69B' on pump 51B thereby locking it in place, the door is latched and knob 84A is screwed tight. The distance between flanges 69B and 69B' on pump 51B generally will be made different than the distance between the corresponding flanges 69A and 69A' on pump 51A, with corresponding differences in prongs 71A and 71B, so that a suction pump cannot be inserted in the PL/IR pump chamber and vice versa. All other replaceable parts listed above are attached and the system is primed and checked for leaks prior to surgery or other use. The system is activated by turning switches 31 and 33 to the desired position and knobs 35, 37, 39 and 41 to the desired settings. Settings are chosen by reading meters 119, 117, 121, and 122 respectively rather than setting the position of the knob; this manner of setting allows much more accurate settings than prior art lavage systems.

When switch 31 is in the lavage position, the adjustment of the pulsations per second knob 37 changes the reciprocation frequency of the motor driving pump 51A. The adjustment of the pulsation per second knob 37 also changes the frequency of the linear reciprocating motor connected to pump 51A. The motor spring load cooperates with the inertia of the reciprocating section to maintain the average pressure of the fluid flow and the fluid flow rate substantially constant even though the frequency has been adjusted either up or down. In the preferred embodiment the response of the amplifier is flat over the range of about 15 to 35 cycles per second while the frequency range available is between approximately 7 to 40 cycles per second. The rate of flow and pressure will stay constant over the former range and substantially constant over the latter range (providing knob 35 is not moved). By the word substantially it is meant that the rate of flow and the pressure is constant within the normal limits of variation of amplifier output with frequency obtainable with off-the-shelf components. Within this range differences in fluid flow are not readily distinguishable. It has been found for example, that knob 35 may be adjusted to a very low flow level where differences in flow might be more readily distinguishable and knob 37 may be adjusted over the full range without any noticeable changes in rate of flow or pressure. Since in prior art devices the rate of flow would change by a factor of 5 or 6 over this range, the improvement provided by the present invention is considerable.

When switch 31 is in the lavage position, the adjustment of knob 35 changes the power amplifier 101 applies to motor 53a. Since the frequency signal does not change (assuming knob 37 is not moved) the motor responds by changing its stroke length. If the power is increased the motor stroke length is increased and if the power is decreased the stroke length is decreased. The change in stroke length changes the amount of fluid pumped in a given stroke and thus changes both the rate of flow and the pressure. The ability of the motor, and thus the reciprocating pump to change its stroke length in response to a change in power provides a much simpler, more reliable and more efficient means of changing the rate of flow or pressure as compared to the prior art. The embodiment described allows the pressure to be varied from about 1 to 75 psi and flow rates to be adjusted up to about 1300 ml/min. Other ranges of pressure and flow rates of course may be obtained.

When knob 31 is placed in the irrigation mode, the control of PL/IR pump 51A passes to knob 39. The frequency is set by the "behind the set" control to about 40 cycles per second. Control 39 is calibrated so that a maximum flow rate of about 200 ml/min. is obtained. This provides a somewhat finer control of the flow rate than that obtained with control 35. In this mode, the rate of flow and pressure may be varied without concern about the frequency setting. The ability to switch between a lavage and irrigation mode with knob 31 permits a surgeon to set desired lavage settings with knobs 35 and 37, to switch to irrigation mode without changing the settings of knobs 35 and 37, and then return to the pulsatile lavage mode with the settings already set at their desired positions. It is noted that the irrigation mode settings can be duplicated in the lavage mode, and thus a principal advantage of having the separate irrigation function is that it permits rapid switching between a selected "steady" flow setting and a selected "pulsatile" setting.

The aspiration function may be selected by turning knob 33 to suction, and then adjusting knob 41 for the desired suction rate or vacuum pressure. The range of suction available in the preferred embodiment is from about 1 to 300 mm of mercury which corresponds to a maximum air flow rate of about 45 liters per minute. The frequency of the suction motor is fixed by the "behind the set" control 116 to between 10 and 40 cycles per second with 25 cycles per second being the preferred frequency setting.

It is noted that the invention is not limited to the range of frequencies, pressures, and flow rates of the preferred embodiment. Electronics are available that provide a much wider range of these parameters. The frequency has been selected to be below 40 cycles per second because frequencies below 40 cycles per second are generally below the threshold of human hearing. This results in an extremely quiet running system. Such low frequencies are possible because the structure of the motor drive permits a wide range of flow rates and pressures to be available even at the low frequencies.

It is noted that because there will be mixtures of air and liquids in suction line 25, the operation of the suction pump 51B will result in cavitation. The pump 51B has been designed to reduce the noise produced by this cavitation. The flexible diaphragm 151 will absorb a certain amount of shock, and the filter 175 also provides a muffling effect.

The setting of the controls will produce the desired type of lavage stream at nozzle 143B and the desired suction at nozzle 143A. The flow of fluid and the suction provided may be controlled directly at the site by use of pinch valves 133 and 135 on lavage handpiece 141. Generally these valves are used for "off" and "on" functions. Valve 133 has been designed so that it will remain in its closed position until it is pushed forward, and valve 135 has been designed so that it will remain at its closed position until serrated arm 137 is lifted to release an open pinch valve 135. In the preferred embodiment, pinch valve 133 is opened by moving pinch valve 133 away from the body of the lavage handpiece 27, while likewise pinch valve 35 moves away from the body 132 of the handpiece 27 when opened. This enables a simultaneous "spreading" movement of pinch valves 133 and 135 to affect a simultaneous opening of both lines 23 and 25. Likewise, when a cessation of operation is desired, a simple squeezing movement of both valves 133 and 135 can be effected. This "outward-inward" operation of the valves facilitates spontaneous operation of the lavage handpiece 27 as a fluid shut-off and attenuation device to augment the system's control board 29.

As described above in connection with the electronics, closure of pinch valve 133 causes the pressure in line 23 to rise, which rise is sensed by transducer 26A and causes the PL/IR motor 53a and pump 51A to shut off. When the valve 133 is released, the pressure in line 23 drops which is again sensed by transducer 26A, which causes the motor 53a and pump 51A to turn on again. In one embodiment potentiometer 35A may be replaced by a dual potentiometer, and one of the pots may be connected to adjust the trip point of the pressure sensing and central circuitry, so that the pressure at which the motor turns off changes as the psi setting is changed; in this embodiment the pressure trip point is maintained about 10 psi above the psi setting of knob 35. This feature provides a remote PL/IR pump control at the lavage site. This remote control is highly efficient when compared to prior art devices, which generally relied totally throttling of the flow to control it. This remote control prevents laboring of the PL/IR pump when 133 is closed, which further reduces the noise of the system and adds significantly to the longevity of the system. It also significantly reduces the risk of bursting pressure lines.

In addition to the shut off of the PL/IR motor by the transducer 26A discussed above, the design of the system also provides a safety feature which limits the maximum pressure in the PL/IR portion of the system and the maximum vacuum in the suction portion of the system. Significantly, this maximum pressure can be adjusted using controls 35, 39 and 41. This feature is provided by the fact that upon application of a given amount of voltage across the coil such as 83 of the motors, a particular magnetic field is set up and consequently a particular force is applied to the piston rods such as 67B. If the fluid pressure acting on the pump, such as 51B, is equal to the force at the piston rod 67B, the piston rod will cease to move. Since the voltage is controllable by knobs 35, 39, and 41, the result is that the maximum pressure and suction provided by the system may be set by these knobs.

After use, the disposable parts mentioned above may be thrown away, or portions of them, such as bag 15 may be thrown away and the other portions resterilized. It is noted that the slow speed at which the linear motors generally operate enables the pumps 51A and 51B to be built without the need for precision tolerances, reinforcing, and/or overly strong materials. This factor contributes significantly to the disposability of the pumps. It is further noted that design of pumps 51A and 51B and the connections to and the supports of the pumps enables the pumps to be quickly and easily replaced by persons unskilled in mechanical assembly, with a minmum of directions. In addition, by producing the fluid lines 19, 21, 23, and 25 already connected to the lavage handpiece 27, the fluid supply bag 15 and the pumps 51A and 51B, and by having the remaining connections restricted by their physical dimensions, erroneous connections by operating personnel are avoided.

After use, the drainage tank 17 may be replaced with a sterilized tank, or the tank 17 may be used with a disposable bag 18, which is shown in FIG. 2. This bag permits sanitary reuse of the same drainage tank 17 without sterilization, and facilitates laboratory analysis of the drained material.

It is a feature of the invention that the independent and precise control of the frequency and the flow rate or pressure permits a much broader use of a lavage system under desired medical conditions. For example, the lavage system of the invention may be utilized on a written prescription basis, for example, in a post-operative stage when the actual care is to be administered by nurses or other para-medical personnel who are not as familiar with the reaction of tissues and wounds to excess pressure, or the need for pressure and flow above a certain level in order to ensure a cleansing action.

A novel lavage system that provides for independent frequency, and pressure and rate of flow controls, provides a broad range of pulsatile lavage, irrigation, and aspiration functions and has numerous other features and advantages has been disclosed. While the above description of the invention has been referenced to a few particular embodiments, it is evident that, now that the advantages of a lavage system with frequency independent of the flow rate or pressure, and the advantages of a variable stroke pump in a lavage system have been disclosed, those skilled in the art can now make numerous uses of, modifications of, and departures from the specific embodiments described herein without departing from the inventive concepts. For example, the inventive concepts could be incorporated into any other type of pump, as for example, a peristaltic type pump.

Or, as another example, the system could be simplified to provide only one of any of the three lavage functions (pulsatile lavage, irrigation, and aspiration), or it may be expanded to include a pulsatile aspiration function, in addition to the other functions, or any combination of the functions. It is also anticipated that other features may be combined with the invention. For example, many different lavage handpieces may be substituted for the handpiece 27, or many different nozzles may be substituted for the nozzles 143A and 143B or, sources of fluid other than container 15 may be provided. It is clear that now that the principles of the invention have been disclosed, most of the system may be replaced by equivalent parts; as for example a wide variety of equivalent electronic circuits are available that will provide the inventive functions; or, for example, the meter 117 and control 37 may be calibrated by period rather than frequency, while meters 119, 114 and 108 and controls 35, 39, and 41 may be labeled and calibrated in terms or torrs, millimeters of mercury, flow rate, absolute power, and a variety of other forms. Consequently, the invention is to be construed as embracing each and every novel feature and novel combination of features within the appended claims.

What I claim is:

1. Medical, dental, or therapeutic lavage apparatus comprising:
    means for producing a pulsating fluid flow; and
    means for varying the pulsation frequency of said pulsating fluid flow while maintaining the pressure of said fluid flow substantially constant;
    means for varying the fluid pressure of fluid flow while maintaining said frequency constant;
    means for fixing said frequency at a predetermined frequency;
    a switch having a first position in which said means for varying the frequency is enabled to control said pulsation frequency, and a second position in which said means for fixing said frequency is enabled to control said pulsation frequency;
    said means for varying the pressure of fluid flow includes:
    a first manually settable control for controlling the pressure of fluid flow; and
    a second manually settable control for controlling the pressure of fluid flow; and
    said switch includes means for switching control of the pressure to said first control when said switch is in said first position and for switching control of the pressure to said second control when said switch is in said second position.

2. The apparatus of claim 1 wherein:
    said means for producing a pulsating fluid flow includes a reciprocating pump;
    said means for varying the frequency comprises a means for varying the frequency of reciprocation of said pump; and
    said means for varying the pressure of fluid flow comprises a means of varying the stroke length of said reciprocating pump.

3. The apparatus of claim 1 wherein said means for producing a pulsating fluid flow includes an electric motor and an amplifier means for applying a power signal to the motor and said means for varying the pulsation frequency while maintaining the pressure of flow constant includes a means for adjusting the gain of the amplifier as the frequency is varied to maintain the amplifier output substantially flat while the pulsation frequency is varied.

* * * * *